(12) United States Patent
Smith et al.

(10) Patent No.: US 9,132,170 B2
(45) Date of Patent: Sep. 15, 2015

(54) COMPOSITIONS AND METHODS FOR TREATING COGNITIVE DEFICITS

(75) Inventors: Gemma Casadesus Smith, Chagrin Falls, OH (US); Brittany Adler, Stanford, CA (US); Mark Yarchoan, Bethesda, MD (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/561,325

(22) Filed: Jul. 30, 2012

(65) Prior Publication Data

US 2013/0190230 A1   Jul. 25, 2013

Related U.S. Application Data

(60) Provisional application No. 61/513,188, filed on Jul. 29, 2011.

(51) Int. Cl.
*A61K 38/00* (2006.01)
*A61K 38/22* (2006.01)
*A61K 45/06* (2006.01)

(52) U.S. Cl.
CPC ............. *A61K 38/22* (2013.01); *A61K 38/2264* (2013.01); *A61K 45/06* (2013.01)

(58) Field of Classification Search
None
See application file for complete search history.

(56) References Cited

U.S. PATENT DOCUMENTS 8,227,408 B2 * 7/2012 Tezapsidis .................... 514/5.8
2009/0181890 A1 * 7/2009 Laugero et al. ................. 514/12

OTHER PUBLICATIONS

Flood et al., Peptides, 1992, 13:577-80.*
Morley et al., Can. J. Physiol. Pharmacol., 1995, 73:1042-6.*

* cited by examiner

*Primary Examiner* — Olga N Chernyshev
(74) *Attorney, Agent, or Firm* — Tarolli, Sundheim, Covell & Tummino LLP

(57) ABSTRACT

A method of treating or preventing cognitive impairment deficits in subjects with age-associated cognitive decline or a dementing illness includes administering to the subject a therapeutically effective amount of amylin, an amylin agonist, or an amylin derivative to treat the cognitive impairment or deficit.

13 Claims, 12 Drawing Sheets

1

COMPOSITIONS AND METHODS FOR TREATING COGNITIVE DEFICITS

RELATED APPLICATION

This application claims priority from U.S. Provisional Application No. 61/513,188, filed Jul. 29, 2011, the subject matter of which is incorporated herein by reference in its entirety.

TECHNICAL FIELD

This application generally relates to compositions and method for enhancing cognitive function and particularly relates to composition and methods of treating or preventing cognitive deficits in subjects with age-associated cognitive decline or a dementing illness.

BACKGROUND

Multiple neurodegenerative diseases, such as but not limited to Alzheimer's disease (AD), are marked by a progressive decline in cognitive function. The mechanisms underlying these diseases remain unclear, and current interventions for such diseases provide only limited and temporary benefit to a subgroup of patients. Therefore, therapy for neurodegenerative disease represents a large unmet medical need and alternative approaches to therapy are needed. Epidemiologic studies have linked metabolic changes and diseases including obesity, insulin resistance, and diabetes with Alzheimer's disease (AD), Parkinson's disease, and related neurodegenerative diseases, and increasing emphasis is being placed on metabolic processes to try to understand the pathogenesis of these diseases. For example, metabolic hormones including leptin and GLP-1 have recently come into focus as potential targets in the treatment of AD. These hormones have been shown to improve cognitive functions in mouse models of AD.

SUMMARY

This application relates to a method of treating or preventing cognitive impairment or deficits in subjects with age-associated cognitive decline or a dementing illness. The method includes administering to the subject a therapeutically effective amount of an amylin, amylin agonist, or an amylin derivative to treat the cognitive impairment or deficit. The age-related cognitive decline or dementing illness is selected from the group consisting of age-associated memory impairment, mild cognitive impairment, Alzheimer's disease, and related dementia.

The amount of the amylin, amylin agonist, or the amylin derivative administered to the subject can be an amount effective to increase cognitive scores; improve memory; slow the progression of dementia; or increase the life expectancy of the affected subject.

In another aspect, a therapeutically effective amount of leptin, a leptin mimic, a leptin derivative or leptin agonist can be administered to the subject in combination with the amylin, amylin agonist, or amylin derivative. The amount of the amylin, amylin agonist, or amylin derivative in combination with leptin, the leptin mimic, the leptin derivative, or leptin agonist administered to the subject is an amount effective to increase cognitive scores; improve memory; slow the progression of dementia; or increase the life expectancy of the affected subject.

In a further aspect, a therapeutically effective amount of an acetylcholinesterase inhibitor can be administered to the subject in combination with the amylin, amylin agonist, or amylin derivative. The amount of the amylin, amylin agonist, or amylin derivative in combination with the acetylcholinesterase inhibitor administered to the subject is an amount effective increase cognitive scores; improve memory; slow the progression of dementia; or increase the life expectancy of the affected subject.

DETAILED DESCRIPTION

Figure 1:
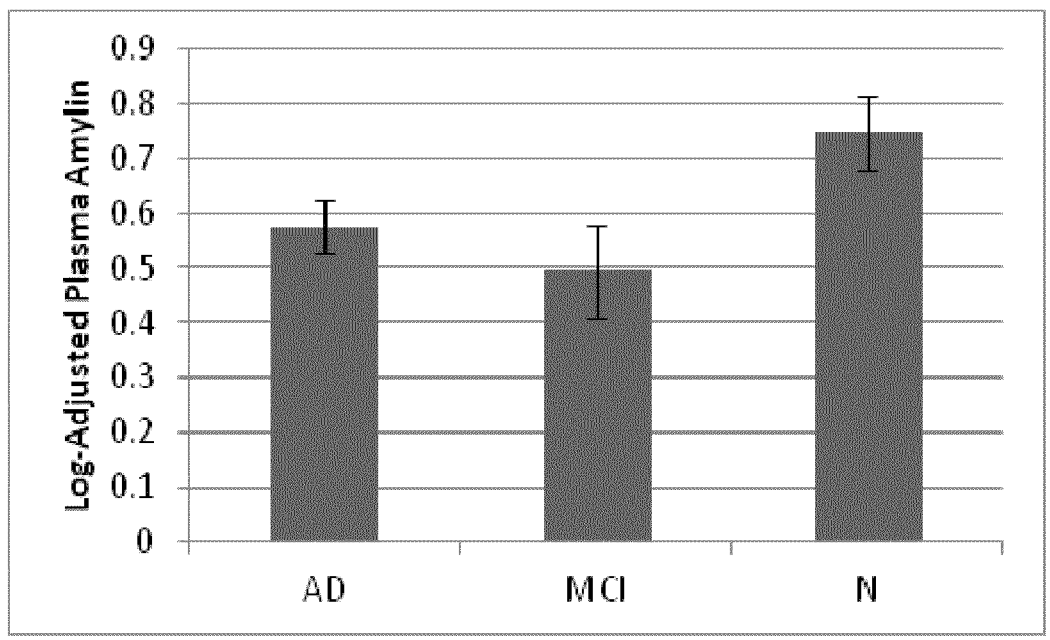
FIG. 1 illustrates a graph showing plasma amylin is significantly reduced in AD and MCI compared to normal aging.

As used herein, the terms "agent" or "drug" denotes a chemical compound, a mixture of chemical compounds, a biological macromolecule, or an extract made from biological materials, such as bacteria, plants, fungi, or animal particularly mammalian cells or tissues that are suspected of having therapeutic properties. The agent or drug may be purified, substantially purified or partially purified.

As used herein, the terms "purified" or "to purify" refer to the removal of one or more contaminants from a sample.

As used herein, the term "partially purified" refers to the removal of a moderate portion of the contaminants of a sample to the extent that the substance of interest is recognizable by techniques known to those skilled in the art as accounting for a measurable amount of the mixture. Preferably, the compound of interest is at least 5% of the total preparation and up to 50% of the total preparation. As used herein, the term "substantially purified" refers to the removal of a significant portion of the contaminants of a sample to the extent that the substance of interest is recognizable by techniques known to those skilled in the art as the most abundant substance in the mixture.

As used herein, the term "agonist" refers to a molecule which, when interacting with a biologically active molecule, causes a change (e.g., enhancement) in the biologically active molecule, which modulates the activity of the biologically active molecule. Agonists include, but are not limited to small molecules, proteins, nucleic acids, carbohydrates, lipids or any other molecules which bind or interact with biologically active molecules. For example, agonists can alter the activity of gene transcription by interacting with RNA polymerase directly or through a transcription factor or signal transduction pathway. Agonists can mimic the action of a "native" or "natural" compound. Agonists may be homologous to these natural compounds in respect to conformation, charge or other characteristics. Thus, agonists may be recognized by, e.g., nuclear receptors. This recognition may result in physiologic and/or biochemical changes within the cell, such that the cell reacts to the presence of the agonist in the same manner as if the natural compound was present.

As used herein, the term "effective amount" means an amount of a compound, material, composition, medicament, or other material that is effective to achieve a particular biological result. Such results include, but are not limited to, one or more of the following: enhancing cognitive function, increasing daytime activity, improving learning (either the rate or ease of learning), improving attention, improving social behavior, improving motor performance, and/or improving cerebrovascular function, particularly in aging subjects. In various embodiments, "effective amount" refers to an amount suitable to prevent a decline in any one or more of the above qualities, or, in certain embodiments, to improve any one or more of the above qualities, for example, cognitive function or performance, learning rate or ability, problem solving ability, attention span and ability to focus on a task or problem, motor function or performance, social behavior, and the like. In other embodiments, an effective amount is suitable to reduce either the extent or rate of decline in a subjects cognitive skills or functioning, and/or the effective amount is suitable to delay the onset of such decline. Such effectiveness may be achieved, for example, by administering the compositions described herein to an individual or to a population. Preferably the prevention, reduction, or delay of such a decline, or the improvement in an individual or population is relative to a cohort, e.g., a control subject or a cohort population that has not received the treatment, or been administered the composition or medicament.

As used herein, the term "cognitive function" refers to the special, normal, or proper physiologic activity of the brain, including one or more of the following: mental stability, memory/recall abilities, problem solving abilities, reasoning abilities, thinking abilities, judging abilities, ability to discriminate or make choices, capacity for learning, ease of learning, perception, intuition, attention, and awareness. "Enhanced cognitive function" or "improved cognitive function" refers to any improvement in the special, normal, or proper physiologic activity of the brain, including one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any means suitable in the art.

As used herein, the term "aging" means being of advanced age such that the subject has exceeded 50% of the average lifespan for its particular species and/or breed within a species.

As used herein, the term "dementia" refers to a decline or a progressive decline in cognitive function due to damage or disease in the brain beyond what might be expected from normal aging.

As used herein, the terms "disease" or "disorder" refer to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

As used herein, the term "subject" refers to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the term "monitoring" as used herein refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As use herein, the term "quantitative data" as used herein refers to data associated with any dataset components (e.g., markers, clinical indicia, metabolic measures, or genetic assays) that can be assigned a numerical value. Quantitative data can be a measure of the level of a marker and expressed in units of measurement, such as molar concentration, concentration by weight, etc.

The term "bodily sample" is used herein in its broadest sense. A bodily sample may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., urine, blood, blood plasma, saliva; and archival samples with known diagnosis, treatment and/or outcome history.

As used herein, the terms "normal" and "healthy" are used herein interchangeably. They refer to an individual or group of individuals who have not shown any symptoms of age-associated cognitive decline or dementing illness. Preferably, the normal individual (or group of individuals) is not on medication affecting age-associated cognitive decline or dementing illness. In certain embodiments, normal individuals have similar sex, age, body mass index as compared with the individual from which the sample to be tested was obtained. The term "normal" is also used herein to qualify a sample isolated from a healthy individual.

As used herein, the terms "control" or "control sample" as used herein refer to one or more biological samples isolated from an individual or group of individuals that are normal (i.e., healthy). The term "control", "control value" or "control sample" can also refer to the compilation of data derived from samples of one or more individuals classified as normal and/or one or more individuals diagnosed with age-associated cognitive decline or dementing illness.

As used herein, the phrase "indicative of an increased risk of age-associated cognitive decline or dementing illness" as used herein, when applied to an amount of amylin in a sample, refers to a level or an amount, which is indicative of an increased risk of age-associated cognitive decline or dementing illness, such that the level is found significantly more often in subjects with age-associated cognitive decline or dementing illness than in patients without age-associated cognitive decline or dementing illness (as determined using routine statistical methods setting confidence levels at a minimum of 95%). Preferably, a level, which is indicative of an increased risk of age-associated cognitive decline or dementing illness, is found in at least about 60% of patients who have age-associated cognitive decline or dementing illness and is found in less than about 10% of subjects who do not have the age-associated cognitive decline or dementing illness. More preferably, a level, which is indicative of an increased risk of age-associated cognitive decline or dementing illness, is found in at least about 70%, at least about 75%, at least about 80%, at least about 85%, at least about 90%, at least about 95% or more in patients who have the age-associated cognitive decline or dementing illness and is found in less than about 10%, less than about 8%, less than about 5%, less than about 2.5%, or less than about 1% of subjects who do not have the age-associated cognitive decline or dementing illness.

As used herein, the term "treatment" is an approach for obtaining beneficial or desired results, including clinical results. "Treating" or "palliating" a disease, disorder, or condition means that the extent, undesirable clinical manifestations of a condition, or both, of a disorder or a disease state are lessened and/or time course of the progression is slowed or lengthened, as compared to not treating the disorder. For purposes of the methods disclosed herein, beneficial or desired clinical results include, but are not limited to, alleviation or amelioration of one or more symptoms, diminishment of extent of disorder, stabilized (i.e., not worsening) state of disorder, delay or slowing of disorder progression, amelioration or palliation of the disorder, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

Embodiments of this application relate to compositions and methods of treating or preventing cognitive impairment or deficits in subjects with age-associated cognitive decline, such as Mild Cognitive Impairment (MCI) and age associated memory impairment, or a dementing illness, such as Alzheimer's disease (AD), Huntington's disease, Parkinson's disease, and the like. The compositions and methods include the use of amylin, an amylin agonist, or an amylin derivative alone or in combination with leptin, a leptin mimic, a leptin derivative, a leptin agonist as well as an acetylcholinesterase inhibitor, RXR agonist, PPARγ agonists, and/or LXR agonists to improve or enhance cognitive function in a subject with age-associated cognitive decline or a dementing illness.

Experiments conducted during development of the composition and methods described herein demonstrate that amylin is a cognitive enhancing drug that can be given alone or in combination with leptin, a leptin mimic, a leptin derivative, a leptin agonist and/or an acetylcholinesterase inhibitor to enhance cognitive function or treat or prevent cognitive dysfunction associated with diseases, such as Alzheimer's disease or age-related cognitive dysfunction (normal or Mild cognitive impairment (MCI)). Accordingly, in some embodiments, amylin, an amylin agonist, or an amylin derivative can be administered to subject alone or in combination with leptin, a leptin mimic, a leptin derivative, a leptin agonist and/or an acetylcholinesterase inhibitor at an amount effective to increase the level of amylin in the blood of the subject to a level comparable to the level of amylin in a normal healthy subject. In other embodiments, amylin, an amylin agonist, or an amylin derivative can be administered to a subject alone or in combination with leptin, a leptin mimic, a leptin derivative, a leptin agonist and/or an acetylcholinesterase inhibitor at an amount effective to (1) reduce the symptoms of the disease sought to be treated and/or (2) induce a change relevant to treating the disease sought to be treated. For any age-associated cognitive decline or deficit, such as Mild Cognitive Impairment, AAMI, or a dementing illness such as Alzheimer's disease, Huntington's disease, Parkinson's disease, and the like, the amount can be effective to: increase cognitive scores; improve memory; slow the progression of dementia; or increase the life expectancy of the affected subject.

In some embodiments, the subject treated with or administered amylin, an amylin agonist, or an amylin derivative alone or in combination with leptin, a leptin mimic, a leptin derivative, a leptin agonist and/or an acetylcholinesterase inhibitor can have a reduced or lower amylin level compared to a normal healthy subject. The subject can also have any number of classic risk factors for age-associated cognitive impairment or dementing illness including obesity, insulin resistance, diabetes, hypertension, and/or an apolipoprotein E4 genotype.

By "amylin" it is meant the human peptide hormone referred to as amylin and secreted from the beta cells of the pancreas, and species variations thereof, examples of which are described in U.S. Pat. No. 5,234,906 and U.S. Patent Application Publication No. 2009/0181890, the contents of which are hereby incorporated by reference. More particularly, amylin is a 37-amino acid polypeptide hormone normally co-secreted with insulin by pancreatic beta cells in response to nutrient intake (see, e.g., Koda et al. (1992) Lancet 339:1179-1180). In this sense, "amylin," "wild-type amylin," and "native amylin," i.e., unmodified amylin, are used interchangeably. Amylin is also sometimes referred to as "IAPP."

By "amylin agonist" it is meant a compound, which elicits a biological activity of amylin, for example, having a potency better than amylin, or within five orders of magnitude (plus or minus) of potency compared to amylin, for example 4, 3, 2, or 1 order of magnitude, when evaluated by art-known measures such as, for example, receptor binding/competition studies as described herein.

In one embodiment, the term amylin agonist refers to a compound which elicits a biological effect similar to that of native amylin, for example a compound (I) having activity in a food intake, gastric emptying, pancreatic secretion, or weight loss assay (PCT Application No. PCT/US2005/004631, filed on Feb. 11, 2005, and incorporated by reference) similar to the native human reference peptide, and/or (2) which binds specifically in a reference receptor assay or in a competitive binding assay with amylin. In one embodiment, the amylin agonists can bind in such assays with an affinity of better than 1 µM, and, in another embodiment, with an affinity of better than 1-5 nM. Such amylin agonists can comprise a polypeptide that includes an active fragment of amylin or a small chemical molecule.

Amylin agonists can also include amylin analogs and amylin derivatives. By "amylin analog" it is meant a peptide whose sequence is derived from that of amylin including insertions, substitutions, extensions, and/or deletions, having at least some amino acid identity to amylin or region of an amylin peptide. Analogs may have at least 50 or 55% amino acid sequence identity with a native amylin, or at least 70%, 80%, 90%, or 95% amino acid sequence identity with a native amylin. In one embodiment, such analogs may comprise conservative or non-conservative amino acid substitutions (including non-natural amino acids and L and D forms). Amylin agonist analogs are analogs as herein described and function as an amylin agonist.

An "amylin derivative" is defined as a molecule having the amino acid sequence of a native amylin or analog, but additionally having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g., branched, cyclic, fused, adamantyl) and N-acyl modifications. Modifications of the terminal carboxy group include, without limitation, the amide, lower alkyl amide, constrained alkyls (e.g., branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated. Human amylin (hAmylin or h-amylin) has the following amino acid sequence: KCNTATCATQRLANFLVHSSNNFGAILSSTNVGSNTY— (SEQ ID NO:1). Rat amylin (rAmylin) has the following sequence: KCNTATCATQRLANFLVRSSNNLGPVLPPTNVGSNTY (SEQ ID NO:2). The use of amylins from any species is contemplated.

Amylin agonists contemplated for use in the methods disclosed herein include those described in U.S. Pat. Nos. 5,686,411, 6,114,304, and 6,410,511, and PCT Application Publication No. WO 93/10146, U.S. Pat. No. 6,610,824; U.S. Pat. No. 5,998,367; U.S. Pat. No. 6,087,334; U.S. Provisional Application No. 60/617,468, filed Oct. 8, 2004; and PCT Application No. PCT/US2005/004631, the contents of which are herein incorporated by reference in their entirety. One specific example of an amylin agonist analog is pramlintide, which is being developed for the treatment for type 1 and 2 diabetes (Baron et al. (2002) Curr. Drug Targets Immune Endocr. Metabol. Disord. 2:63-82) and has recently been approved by the FDA for such use.

In some embodiments, an amylin agonist can include a compound comprising the amino acid sequence KCNTATCVLGRLSQELHRLQTYPRTNTGSNTY (SEQ ID NO: 3).

Derivatives of the agonists and analogs are also included within the methods provided in which the stereochemistry of individual amino acids may be inverted from (L)/S to (D)/R at one or more specific sites. Also included within the methods provided are the agonists and analogs modified by glycosylation of Asn, Ser and/or Thr residues. Compounds useful in the methods provided may also be biologically active fragments of the peptides (native, agonist, analog, and derivative) herein described.

Agonist and analogs of amylin that contain less peptide character are included within the methods provided. Such peptide mimetics may include, for example, one or more of the following substitutions for —CO—NH— amide bonds: depsipeptides (—CO—O—), iminomethylenes (—CH$_2$—NH—), trans-alkenes (—CH═CH—), β-enaminonitriles (—C(═CH—CN)—NH—), thioamides (—CS—NH—), thiomethylenes (—S—CH$_2$— or —CH$_2$—S—), methylenes (—CH$_2$—C$_2$—) and retro-amides (—NH—CO—).

Compounds for use in the methods provided can form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). In certain embodiments, the compounds form acetate, hydrochloride, and trifluoroacetate salts.

Amylin agonists useful in the compositions and methods provided herein may also include fragments of amylin and its analogs as described above as well as those described in EP 289287, the contents of which are herein incorporated by reference. Amylin agonists analogs may also be compounds having at least 60, 65, 70, 75, 80, 85, 90, 95, or 99% amino acid sequence identity to SEQ ID NO:1, or any of the amylin analogs specifically described herein having amylin activity. Amylin agonists also include small chemical molecules and non-peptide molecules, for example those based on small molecule chemistry. In some embodiments, amylin agonists are not small chemical molecules.

"Amylin activity" as used herein may include at least one of the activities known in the art as described below. Amylin activity may also include the ability of amylin to modulate the stress response, affect GC and/or affect CFR activity in a body. Amylin agonist analogs also include insertions, deletions, extensions, truncations, and/or substitutions in at least one or more amino acid positions of SEQ ID NO:1 or any of the amylin analogs specifically described herein. The number of amino acid insertions, deletions, or substitutions may be at least 5, 10, 15, 20, or 25 amino acid insertions, deletions, or substitutions. The number of amino acid insertions, deletions, or substitutions may be not more than 5, 10, 15, 20, 25, or 30 amino acid insertions, deletions, or substitutions. Insertions, extensions, or substitutions may be with other natural amino acids, synthetic amino acids, peptidomimetics, or other chemical compounds.

In general, amylin agonists or amylin agonist analogs are recognized as referring to compounds which, by directly or indirectly interacting or binding with one or more receptors, mimics an action of amylin. They may also be referred to as amylinomimetics.

Activity as amylin agonists and/or analogs can be confirmed and quantified by performing various screening assays. Methods of testing compounds for amylin activity are known in the art. Exemplary screening methods and assays for testing amylin agonists are described in U.S. Pat. Nos. 5,264,372 and 5,686,411, which are incorporated herein by reference.

Amylin agonists or derivatives described herein may be prepared using standard solid-phase peptide synthesis techniques, for example using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents, such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. N-protecting groups are well known in the art, with t-butyloxycarbonyl (tBoc) and fluorenylmethoxycarbonyl (Fmoc) being preferred herein. Other methods of synthesizing or expressing amylin and amylin agonists and purifying them are known to the skilled artisan.

The amylin, amylin agonists, amylin analogs, and amylin derivatives may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang et al. (1988) Journal of Parenteral Science and Technology Technical Report No. 10, Supp. 42:2S.

In general, the amylin, amylin agonists, amylin analogs, and amylin derivatives may be formulated into a stable, safe pharmaceutical composition for administration to a subject. Pharmaceutical formulations contemplated for use in the methods described herein may comprise approximately 0.01 to 6.0% (w/v), or 0.05 to 1.0%, of the compound; approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl-, ethyl-, propyl- and butyl-parabens and phenol. Such a preservative is generally included if the formulated peptide is to be included in a multiple use product.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation provided herein.

In one embodiment, the liquid pharmaceutical formulations are intended for parenteral administration. Suitable routes of administration include intramuscular, intravenous, subcutaneous, intradermal, intraarticular, intrathecal and the like. The subcutaneous route of administration is one particular route. Mucosal delivery is also particularly suitable. These mucosal routes include, but are not limited to, oral, nasal, sublingual, pulmonary and buccal routes which may include administration of the peptide in liquid, semi-solid or solid form. Administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The amylin, amylin agonists, amylin analogs, and amylin derivatives may be provided in dosage unit form containing an amount of the compound that will be effective in one or multiple doses to treat or help in treating the psychiatric disease and/or unwanted side effects of the psychiatric treatment/medication. As will be recognized by those in the field, an effective amount of therapeutic agent will vary with many factors including the age and weight of the patient, the patient's physical condition, the condition to be treated, and other factors.

However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 µg to 1 mg of the compound per dose. Thus, exemplary doses may be 30, 60, 120, 240, or 360 µg of the compound per dose. The doses per day may be delivered in discrete unit doses or provided continuously in a 24 hour period, or any portion of that 24 hour period. The number of doses per day may be from 1 to about 4 doses per day, although it could be more. Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c may be about 6 µg to about 16 or 24 mg per day.

In other embodiments, amylin can be administered to the subject by administering or transplanting cells to the subject that express amylin. By way of example, cell expressing amylin can be administered to the subject using pancreatic islet cell transplantation (ICT) in which amylin expressing beta cells are transplanted to the subject. Current pancreatic islet transplantation techniques are based on the enzymatic isolation of the pancreatic islets of Langerhans from an organ procured from a cadaveric donor. The islets obtained are injected into the liver of the recipient via percutaneous catheterization of the portal venous system. This procedure allows the selective transplantation of an amylin-producing cell population avoiding open surgery as well as the transplantation of the duodenum and the exocrine pancreas and their related morbidity.

There are currently two trends in islet cell transplantation, using the immediate and delayed infusion approach. The immediate transplantation focuses on the use of the shortest time possible between islet isolation and islet infusion. An alternative method implies short-term culture of the islets after the isolation and before transplantation. This ensures increased purity of the islet isolate while it does not affect the viability and the function of the islets and seems to yield good results while the procedure is performed in a semi-elective setting Different anatomic locations can be used for the engrafting of the islet cells. Currently, the portal vein is the preferred site of infusion, given the relative ease of access, the high venous flow with a double circulation system (arterial and portal venous) of the liver. The liver has a good regenerative capacity and is one of the major sites of insulin action. The liver site also seems to confer some immunological privilege to the islets.

In other embodiments, the transplanted cells can include islet progenitor cells, such as beta-cell progenitor cells. Islet progenitor cells can include embryonic pancreatic cells obtained from a mammal. The embryonic pancreatic cells can be cultured prior to transplantation to promote differentiation into mature beta cells that can readily express a therapeutically effective amount of amylin upon transplantation.

In another embodiment of the application, a composition containing leptin, a leptin mimic, a leptin derivative, or a leptin agonist can be administered in combination with the amylin, amylin agonists, amylin analogs, and amylin derivatives to improve or enhance cognitive function in a subject with age-associated cognitive decline or a dementing illness.

The terms "leptin mimic, leptin mimetic or leptin peptidomimetic" are used interchangeably herein to refer to a leptin derivative comprising a functional domain of the leptin protein, alone or in combination with another molecule, which will produce a biological effect, namely the effect of modulating amyloid peptide levels in a subject. More specifically, a peptidomimetic is a compound containing non-peptidic structural elements capable of mimicking or antagonizing (meaning neutralizing or counteracting) the biological action(s) of a natural parent peptide. Particularly useful for the present invention is a peptidomimetic incorporating the portion of leptin mediating activity, such as decreasing amyloid peptide levels, that is of a size small enough to penetrate the blood-brain barrier. Likewise, a leptin agonist is a compound capable of activating the leptin receptor and/or downstream effectors and modulating amyloid peptide levels in a subject.

In some embodiments, compositions containing leptin, a leptin mimic, a leptin derivative, a leptin agonist or a pharmaceutically acceptable salt thereof may be administered orally, buccally, parenterally, intranasally, rectally, or topically.

In other embodiments, the compositions containing leptin, a leptin mimic, a leptin derivative, a leptin agonist or a pharmaceutically acceptable salt thereof may be in the form of a sterile injectable aqueous or oleaginous suspension. Injectable preparations, such as sterile injectable aqueous or oleaginous suspensions, may be formulated according to the known art using suitable dispersing or wetting agents and suspending agents.

Additional compositions containing leptin, a leptin mimic, a leptin derivative, a leptin agonist or a pharmaceutically acceptable salt thereof can be prepared readily using technology is known in the art, such as that which is described in Remington's Pharmaceutical Sciences, 18th or 19th editions, published by the Mack Publishing Company of Easton, Pa., which is incorporated herein by reference.

In further embodiments of the specification, an acetylcholinesterase inhibitor can be administered to the subject in combination with the amylin, amylin agonist, or amylin derivative to improve or enhance cognitive function in a subject with age-associated cognitive decline or a dementing illness.

Acetylcholinesterase inhibitors that can be administered in combination with the amylin, amylin agonist, or amylin derivative can include those currently used or tested for treating dementia, such as 1,2,3,4-tetrahydro-9-acridinamine (tacrine), 9-amino-2,3,5,6,7,8-hexahydro-1H-cyclopenta[b] quinoline (ipidacrine); (+)-2,3-dihydro-5,6-dimethoxy-2-[[1-(phenylmethyl)-4-piperidinyl]methyl-1]-1H-inden-1-one (donepezil) and its pharmaceutically acceptable salts, in particular the hydrochloride, 3-[2-(1-benzyl-4-piperidyl) ethyl]-5,7-dihydro-6H-pyrrolo[3,2-f]-1,2-benz-isoxazol-6-one (icopezil) and its pharmaceutically acceptable salts, in particular the maleate, 3-[1-benzylpiperidin-4-yl]-1-(2,3,4,5-tetrahydro-1H-1-benzazepin-8-yl)propan-1-one (zanapezil) and its pharmaceutically acceptable salts, in particular the fumarate, (S)—N-Ethyl-N-methyl-3-[1-(dimethylamino)

ethyl]-phenyl carbamate (rivastigmine) and its pharmaceutically acceptable salts, in particular the hydrogen (2R,3R)-tartrate, 4aS,6R,8aS-3-methoxy-11-methyl-4-a,5,9,10,11,12-hexahydroxy-6H-benzofuro[3-a,3,2-e,f]benzazepin-6-ol (galantamine) and its pharmaceutically acceptable salts; (1R,9S,13E)-1-amino-13-ethylidene-11-methyl-6-azatricyclo [7.3.1.0$^{2,7}$-]trideca-2(7),3,10-trien-5-one (huperzine A) and phenserine and its analogs encompassed by the general formula I:

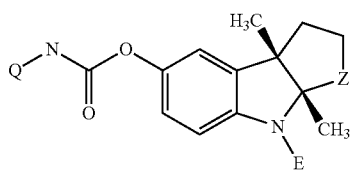

wherein Q is a phenyl group optionally substituted with a (C$_1$-C$_4$)alkyl or with a methoxy group, Z is an oxygen or sulfur atom or a N-E' radical, E and E', independently, are hydrogen or a methyl group optionally substituted with a phenyl or benzyl group; and pharmaceutical acceptable salts thereof, all of which are disclosed in U.S. Patent Application Publication No. 2011/0071135, which is incorporated by reference in its entirety.

Examples of acetylcholinesterase inhibitors of formula (I), described in U.S. Pat. No. 6,683,105, are phenserine (Q=phenyl; E=CH$_3$; Z=N—CH$_3$); (−)—N$^1$,N$^8$-bisnorphenserine (Q=phenyl; E=H; Z=N—H); 4'-methoxyphenserine (Q=4'-methoxyphenyl; E=CH$_3$; Z=N—CH$_3$); (−)—N$^1$,N$^8$-bisbenzylnorphenserine (Q=phenyl; E=CH$_2$C$_6$H$_5$; Z=N—CH$_2$C$_6$H$_5$); tolserine (Q=o-tolyl; E=CH$_3$; Z=N—CH$_3$); N$^1$-benzylnortolserine (Q=o-tolyl; E=CH$_3$; Z=N—CH$_2$—C$_6$H$_5$); N$^1$-phenethylnortolserine (Q=o-tolyl; E=CH$_3$; Z=N—CH$_2$—CH$_2$—C$_6$H$_5$); N$^1$-nortolserine (Q=o-tolyl; E=CH$_3$; Z=N—H); N$^8$-benzylnortolserine (Q=o-tolyl; E=N—CH$_2$—C$_6$H$_5$; Z=N—CH$_3$); N$^8$-phenethylnortolserine (Q=o-tolyl; E=N—CH$_2$—CH$_2$—C$_6$H$_5$; Z=N—CH$_3$); N$^1$-nortolserine (Q=o-tolyl; E=H; Z=N—CH$_3$); N$^1$,N$^8$-bisnortolserine (Q=o-tolyl; E H; Z=N—H); (−)—N$^1$,N$^8$-bisbenzylnortolserine (Q=o-tolyl; E=CH$_2$C$_6$H$_5$; Z=N—CH$_2$C$_6$H$_5$); cymserine (Q=p-isopropylphenyl; E=CH$_3$; Z=N—CH$_3$); N$^1$-benzylnorcymserine (Q=p-isopropylphenyl; E=CH$_3$; Z=N—CH$_2$—C$_6$H$_5$); N$^1$-phenethylnorcymserine (Q=p-isopropylphenyl; E=CH$_3$; Z=N—CH$_2$—CH$_2$—C$_6$H$_5$); N$^1$-norcymserine (Q=p-isopropylphenyl; E=CH$_3$; Z=N—H); N$^8$-benzylnorcymserine (Q=p-isopropylphenyl; E=N—CH$_2$—C$_6$H$_5$; Z=N—CH$_3$); N$^8$-phenethylnorcymserine (Q=p-isopropylphenyl; E=N—CH$_2$CH$_2$C$_6$H$_5$; Z=N—CH$_3$); N$^8$-norcymserine (Q=p-isopropylphenyl; E=H; Z=N—CH$_3$); N$^1$,N$^8$-bisnorcymserine (Q=p-isopropylphenyl; E=H; Z=N—H); (−)—N$^1$,N$^8$-bisbenzylnorcymserine (Q=p-isopropylphenyl; E=CH$_2$C$_6$H$_5$; Z=N—CH$_2$C$_6$H$_5$); thiacymserine (Q=p-isopropylphenyl; E=CH$_3$; Z=S); thiatolserine (Q=o-tolyl; E=—CH$_3$; Z=S).

Donepezil hydrochloride, rivastigmine hydrogen (2R,3R)-tartrate and galantamine hydrobromide are the most used acetyl choline esterase inhibitors, phenserine tartrate and huperzine A also being advantageous acetylcholinesterase inhibitors, for improving dementias of Alzheimer's type.

Among the acetylcholinesterase inhibitors mentioned above, when given in IR preparations, phenserine, as tartrate, is administered at a daily dose of from 45 mg to 90 mg, advantageously from 60 mg to 90 mg, up to 120 mg; tacrine is administered at daily doses of from 240 mg to 320 mg, advantageously of from 320 mg to 480 mg, up to 640 mg; donepezil, as hydrochloride, is administered at daily doses of from 15 mg to 30 mg, advantageously from 20 mg to 30 mg, up to 40 mg; rivastigmine, as hydrogen tartrate, is administered at daily doses of from 18 mg to 36, advantageously from 24 mg to 36 mg, up to 48 mg; galantamine, as hydrobromide, is administered at daily doses of from 36 mg to 72 mg, advantageously from 48 mg to 72 mg, up to 96 mg; huperzine A is administered at a daily dose of from 0.2 mg to 0.8 mg, advantageously from 0.6 mg to 0.8 mg, up to 1.2 mg.

It will be appreciated that the dose, amount, and/or quantity of the pharmaceutical compositions described above, which are administered to the subject can depend on the specific amylin, amylin agonist, or amylin derivative or optionally leptin, leptin mimic, leptin derivative, leptin agonist, and/or acetylcholinesterase inhibitors selected. It will also be appreciated that the dosage amounts used will depend on the potency of the specific amylin, amylin agonist, or amylin derivative or optionally leptin, leptin mimic, the leptin derivative, leptin agonists and/or acetylcholinesterase inhibitors and the therapeutic regimen employed.

In another aspect, the amylin, amylin agonist, or the amylin derivative when administered in combination with the leptin, the leptin mimic, the leptin derivative, leptin agonist and/or acetylcholinesterase inhibitors to the subject can be at an amount or dosage to achieve a therapeutic effect that is substantially less (i.e., subtherapeutic dose or amount) than the amount or dose that would be required to achieve a therapeutic effect if each compound was administered alone. Co-administration of the amylin, amylin agonist, or the amylin derivative and leptin, the leptin mimic, the leptin derivative, the leptin agonist and/or acetylcholinesterase inhibitors to the subject can also mitigate resistance to one single agent. Such resistance results either in the requirement for higher dosages of the drug and/or the renewed symptoms. Therefore, there is a practical upper limit to the amount that a subject can receive. However, if two or more agents are used in concert, the dosage of any single drug can be lowered. This is beneficial to the patient since using lower levels of therapeutic agents is generally safer for the patient. Additionally, cells are less likely to generate resistance to the combination of drugs as they are to a single drug. Thus in some aspects of the present invention, the compositions described herein can be administered to a subject at a subtherapeutic level.

The present invention is not limited by the order in which the amylin, amylin agonist, or the amylin derivative or optionally leptin, the leptin mimic, the leptin derivative, and/or acetyl choline esterase inhibitors are administered. In one embodiment, the amylin, amylin agonist, or the amylin derivative or optionally leptin, the leptin mimic, the leptin derivative, and/or acetyl choline esterase inhibitors are administered sequentially. In another embodiment, the amylin, amylin agonist, or the amylin derivative or optionally leptin, the leptin mimic, the leptin derivative, and/or acetyl choline esterase inhibitors are administered as a combined formulation.

In still further embodiments, the amylin, amylin agonist, or the amylin derivative or optionally leptin, the leptin mimic, the leptin derivative, and/or acetyl choline esterase inhibitors can be administered in combination with an RXR agonist, PPARγ agonist, and/or LXR agonist. It has been previously shown that PPARγ and LXRs act in concert to regulate lipid metabolism and ApoE expression. It was also found that administration of RXR agonists, such as Bexarotene, to a subject can drive expression of LXR target genes (ABCA1, ABCG1, ApoE) and PPARγ target genes, which can promote the proteolytic degradation of beta amyloid (Aβ) in neuronal cells. Moreover, it was found that RXR agonists, such as Bexarotene, act additively or synergistically to enhance the actions of LXR agonists or PPARγ agonists in treating Alzheimer's and neurodegenerative disorders or injuries. For example, ligation of both LXR and RXR results in a synergistic increase in the expression of ApoE and Aβ clearance from cells as well as ameliorates the behavioral impairments in in vivo models of Alzheimer's disease.

The RXR agonist can include known RXR agonists that are described in, for example, the following U.S. patents and patent applications, which are incorporated by reference herein: U.S. Pat. Nos. 5,399,586, 5,466,861, 5,780,676, and 5,801,253; U.S. patent application Ser. Nos. 07/809,980, 08/003,223, 08/027,747, 08/045,807, 08/052,050, 08/052,051, 08/179,750, 08/366,613, 08/480,127, 08/481,877, 08/872,707, and 08/944,783. See also, WO 93/11755, WO 93/21146, WO 94/15902, WO94/23068, WO 95/04036, and WO 96/20913.

Other RXR agonists that can be used in the present invention can include RXR agonists described for example, in the following articles: Boehm et al. J. Med. Chem. 38:3146 (1994), Boehm et al. J. Med. Chem. 37:2930 (1994), Antras et al., J. Biol. Chem. 266:1157-61 (1991), Salazar-Olivo et al., Biochem. Biophys. Res. Commun. 204: 10 257-263 (1994), and Safanova, Mol. Cell. Endocrin. 104:201 (1994). Such compounds may be prepared according to methods known in the art as described in the aforementioned references, as well as in M. L. Dawson and W. H. Okamura, Chemistry and Biology of Synthetic Retinoids, Chapters 3, 8, 14 and 16, CRC Press, Inc., Florida (1990); M. L. Dawson and P. D. Hobbs, The Retinoids, Biology, Chemistry and Medicine, M. B. Sporn et al., Eds. (2nd ed.), Raven Press, New York, N.Y., pp. 5-178 (1994); Liu et al., Tetrahedron, 40:1931 (1984); Cancer Res., 43:5268 (1983); Eur. J. Med. Chem. 15:9 (1980); Allegretto et al., J. Bio. Chem., 270:23906 (1995); Bissonette et al., Mol. Cell. Bio., 15:5576 (1995); Beard et al., J. Med. Chem., 38:2820 (1995), Koch et al., J. Med. Chem., 39:3229 (1996); and U.S. Pat. Nos. 4,326,055 and 4,578,498.

In some aspects of the invention, the RXR agonists can include LGD1069 (also known as Bexarotene), LGD100268, and LGD100324. The structures of RXR agonists designated LGD1069, LGD100268, and LGD100324 are shown below, and the synthesis of these compounds is described in U.S. Pat. Nos. 7,655,699 and 5,780,676. The synthesis of compounds LGD1069, LGD100268, and LGD100324 is also described in, e.g., WO 94/15902 and Boehm et al., J. Med. Chem. 38(16):3146 (1994). In another aspect of the present invention, the RXR agonist can include an agent disclosed in U.S. Pat. No. 7,348,359 and/or WO 11/103,321.

In some embodiments, the PPARγ agonists can include, for example, prostaglandin J2 (PGJ2) and analogs thereof (e.g., A2-prostaglandin J2 and 15-deoxy-2,4-prostaglandin J2), members of the prostaglandin D2 family of compounds, docosahexaenoic acid (DHA), and thiazolidinediones (e.g., ciglitazone, troglitazone, pioglitazone and rosiglitazone).

In addition, such PPARγ agonists can include, but are not limited to, L-tyrosine-based compounds, farglitazar, GW7845, indole-derived compounds, indole 5-carboxylic acid derivatives and 2,3-disubstituted indole 5-phenylacetic acid derivatives. It is appreciated that most of the PPARγ agonists exhibit substantial bioavailability following oral administration and have little or no toxicity associated with their use (See, e.g., Saltiel and Olefsky, Diabetes 45:1661 (1996); Wang et al., Br. J. Pharmacol. 122:1405 (1997); and Oakes et al., Metabolism 46:935 (1997)). It will be appreciated that the present invention is not limited to above-identified PPARγ agonists and that other identified PPARγ agonists can also be used.

PPARγ agonists that can be used for practicing the present invention, and methods of making these compounds, are disclosed in WO 91/07107; WO 92/02520; WO 94/01433; WO 89/08651; WO 96/33724; WO 97/31907; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; 5,260,445; 5,814,647; 5,902,726; 5,994,554; 6,294,580; 6,306,854; 6,498,174; 6,506,781; 6,541,492; 6,552,055; 6,579,893; 6,586,455, 6,660,716, 6,673,823; 6,680,387; 6,768,008; 6,787,551; 6,849,741; 6,878,749; 6,958,355; 6,960,604; 7,022,722; and U.S. Applications 20030130306, 20030134885, 20030109579, 20030109560, 20030088103, 20030087902, 20030096846, 20030092697, 20030087935, 20030082631, 20030078288, 20030073862, 20030055265, 20030045553, 20020169192, 20020165282, 20020160997, 20020128260, 20020103188, 20020082292, 20030092736, 20030069275, 20020151569, and 20030064935.

Specific examples of PPARγ agonist compounds of the present invention are given in the following list: (+)-5[[4-[(3,4-dihydro-6-hydroxy-2,5,7,8-tetramethyl-2H-1-benzopyran-2-yl)methoxy]phenyl]methyl]-2,4thiazolidinedione; (troglitazone); 5-[4-[2-(5-ethylpyridin-2-yl)ethoxyl]benzyl] thiazolidine-2,4-dione; (pioglitazone); 5-[4-[(1-methylcyclohexyl) methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino] ethoxy]benzyl]-5-methylthiazolidine-2,4-dione; 5-[4-[2-[2,4dioxo-5-phenylthiazolidine-3-yl)ethoxy]benzyl] thiazolidine-2,4-dione; 5-[4-[2-[(N-methyl-N (phenoxycarbonyl)amino]ethoxy]benzyl]thiazolidine-2,4-dione; 5-[4-[2-phenoxyethoxy)benzyl]thiazolidine-2,4-dione; 5-[4-[2-(4-chlorophenyl)ethylsulfonyl]benzyl] thiazolidine-2,4-dione; 5-[4-[3-(5-methyl-2-phenyloxazol-4-yl)propionyl]benzyl]thiazolidine-2,4-dione; 5-[[4-(3-hydroxyl-methylcyclohexyl)methoxy]benzyl]thiazolidine-2,4-dione; 5-[4-[2-(5-methyl-2-phenyloxazol-4-yl)ethoxyl] benzyl]thiazolidine-2,4-dione; 5-[(2-benzyl-2,3-dihydrobenzopyran)-5-ylmethyl]thiazolidine-2,4-dione; (englitazone); 5-[[2-(2-naphthylmethyl)benzoxazol]-5-ylmethyl]thiazolidine-2,4-dione; 5-[4-[2-(3-phenylureido) ethoxyl]benzyl]thiazolidine-2,4-dione; 5-[4-[2-(N-benzoxazol-2-yl)-N-metholamino]ethoxy]benzyl]thiazolidine-2,4-dione; 5-[4-[3-(5-methyl-2-phenyloxazol-4-yl)propionyl] benzyl]thiazolidine-2,4-dione; 5-[2-(5-methyl-2-phenyloxazol-4-ylmethyl)benzofuran-5-ylmethyl] oxazolidine-2,4-dione; 5-[4-[2-(N-methyl-N-(2-pyridyl) amino]ethoxy]benzyl]thiazolidine-2,4-dione (rosiglitazone); and 5-[4-[2-(N-(benzoxazol-2-yl)-N-methylamino]ethoxy] benzyl]oxazolidine-2,4-dione.

LXR agonists that can be used herein, and methods of making these compounds, are disclosed in PCT WO/03082198A2. In one aspect of the invention, the LXR agonists are selected from those disclosed in International Patent Applications WO 01154759 (Tularik Inc. US), PCT/US01127622 (SmithKline Beecham plc UK), WO 01141704 (Merck & CO., INC) and WO97/28137 (Merck & CO., INC).

In some embodiments, the LXR agonist comprises a compound disclosed in international Patent Application WO 00/54759, international Patent Application PCT/US01/27622 (SmithKline Beecham), U.S. Provisional application Ser. Nos. 09/368,427, 60/368,425 and 60/368,426, each filed Mar.

27, 2002, international Patent Application WO 01/41704 (Merck & Co., Inc.), International Patent Application WO97/28137 (Merck & Co.), along with methods for making them.

The RXR agonists, PPARγ agonists, and the LXR agonists of described herein are capable of further forming both pharmaceutically acceptable acid addition and/or base salts.

Another embodiment of this application relates to a method of detecting, monitoring, or assessing the age-associated cognitive decline or a dementing illness in a subject or an increased risk of age-associated cognitive decline or a dementing illness in a subject. The diagnostic method is able to readily diagnose age-associated cognitive decline or a dementing illness in a subject or an increased risk of age-associated cognitive decline or a dementing illness using a bodily sample that is obtained form the subject by non-invasive or minimally invasive methods. The bodily sample can include, for example, bodily fluids, such as blood, serum, or plasma, that are obtained by minimally invasive methods.

It was found that low plasma amylin levels is significantly associated with age-associated cognitive impairment or dementing illness. The association between low plasma amylin and age-associated cognitive impairment or dementing illness is unexpected because amylin levels are positively associated with a number of classic risk factor for Alzheimer's disease including obesity, insulin resistance, diabetes, and hypertension. Amylin was also found to be significantly associated with another classic risk factor of Alzheimer's disease, apolipoprotein E4 genotype.

Embodiments of the application also relate to methods for monitoring the response of a subject to treatment of age-associated cognitive decline or a dementing illness and to a method of monitoring the pathogenesis of age-associated cognitive decline or a dementing illness.

The subject may be any human or other animal to be tested for age-associated cognitive decline or a dementing illness. The subject may be an "apparently healthy" subject. "Apparently healthy", as used herein, means individuals who have not been previously diagnosed with age-associated cognitive decline or a dementing illness and/or who have not been previously diagnosed as having any signs or symptoms indicating the presence of age-related associated cognitive decline or a dementing illness. Additionally, apparently healthy subjects may include those individuals having low or no risk for developing age-associated cognitive decline or a dementing illness. In addition to apparently healthy subjects, subjects may include individuals having an elevated risk of developing age-associated cognitive decline or a dementing illness. Subjects having an elevated risk of developing age-associated cognitive decline or a dementing illness can include, for example, middle-aged or senior individuals with diabetes, obesity, insulin resistance, hypertension and/or individuals with the apolipoprotein E4 genotype.

In the method of determining or assessing the age-associated cognitive decline or a dementing illness or a risk thereof in the subject, a bodily sample is obtained from the subject. The bodily sample can include biological fluids from the subject, such as whole blood samples and samples of blood fractions including, but not limited to, serum and plasma. The bodily sample may be fresh blood or stored blood (e.g., in a blood bank) or blood fractions. The sample may be a blood sample expressly obtained for the assays described herein, or a blood sample obtained for another purpose, which can be sub-sampled for the assays described herein.

Where, for example, the bodily sample is whole blood, the whole blood may be obtained from the subject using standard clinical procedures. Additionally, where the sample is plasma, the plasma may be obtained from whole blood samples by centrifugation of anti-coagulated blood. Such process provides a buffy coat of white cell components and a supernatant of the plasma.

In some embodiments, a bodily sample comprising whole blood may first be taken from the subject and then processed to plasma and stored frozen (e.g., at about −80 C.) until needed for analysis. Alternatively, where the bodily sample is serum, the serum may be obtained by centrifugation of whole blood samples that have been collected in tubes that are free of anti-coagulant. The blood is permitted to clot prior to centrifugation. The yellowish-reddish fluid that is obtained by centrifugation is the serum.

After obtaining the bodily sample (e.g., blood, serum, plasma), the level of amylin in the bodily sample is detected, measured, and/or quantified. The level of amylin in the bodily sample can be detected and/or quantified using an immunoassay, such as an enzyme-linked immunoabsorbent assay (ELISA). In an ELISA, antibodies specific to a particular antigen are used to detect the presence of, or measure the amount of, a particular molecule.

An ELISA typically comprises the steps of contacting a sample taken from a subject with one or more antibodies, and then assaying for the formation of a complex between the antibody and a protein or peptide in the sample. For ease of detection, the antibody can be attached to a substrate such as a column, plastic dish, matrix, or membrane, such as nitrocellulose. The sample may be untreated, subject to precipitation, fractionation, separation, or purification before combining with the antibody.

In an ELISA, interactions between the antibody or antibodies in the sample and the protein(s) or peptide fragment(s) are detected by radiometric, colorimetric, or fluorometric means, size-separation, or precipitation. In one example, detection of the antibody-protein or peptide complex is by addition of a secondary antibody coupled to a detectable tag, such as an enzyme, fluorophore, or chromophore. In the present invention, tetramethyl-benzidine substrate may be added to the assay and color develops in proportion to the bound analyte. The color development may then be stopped and color intensity measured in a microplate reader at 450 nm.

It will be appreciated that additional assays can be used to detect and/or quantify amylin in the bodily sample. These assays can include radioimmunoassays, both solid and liquid phase, fluorescence-linked assays, and competitive immunoassays as well as other assays, such as mass spectrometry (MS)-based methods (e.g., liquid chromatography MS and electrospray ionization MS). MS based methods may be useful for detecting and/or quantifying the level of amylin.

The assayed level of amylin can be correlated with age-associated cognitive decline or a dementing illness by comparing the detected level of amylin with a predetermined value. In one aspect, the predetermined value can be based upon the level of amylin in comparable samples obtained from the general population or from a select population of human subjects. For example, the select population may be comprised of apparently healthy subjects. In other words, such individuals, if examined by a medical professional, would be characterized as healthy and free of symptoms of age-associated cognitive decline or a dementing illness.

The predetermined value can be related to the value used to characterize the level of amylin in a bodily sample obtained from a subject. Thus, if the level of amylin is an absolute value, such as the units per liter of amylin in plasma, the predetermined value is also based upon the units per liter of amylin in plasma in the general population or a select population of human subjects. Similarly, if the level of amylin is a representative value such as an arbitrary unit obtained by a radioimmunoassay, for example, the predetermined value is also based on the representative value.

The predetermined value can take a variety of forms. The predetermined value can be a single cut-off value, such as a median or mean. The predetermined value can be established based upon comparative groups, such as the level of amylin in one defined group being double the level of systemic marker in another defined group. The predetermined value can be a range, for example, where the general population is divided equally (or unequally) into groups, or into quadrants, the lowest quadrant being individuals with the lowest levels of amylin, and the highest quadrant being the individuals with the highest levels of amylin.

Predetermined values of amylin, such as mean levels, median levels, or "cut-off" levels, for example, may be established by assaying a large sample of individuals in the general or a select population using a statistical model, such as the predictive value method for selecting a positivity criterion or receiver operator characteristic curve, that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co., Malvern, Pa.

The presence or absence of age-associated cognitive decline or a dementing illness in a subject may be determined by comparing a predetermined value of amylin in a bodily sample taken from a subject. A predetermined value of amylin may first be assayed from a bodily sample taken from an apparently healthy subject or population of apparently healthy subjects (as described above). After determining the predetermined value, a bodily sample may be obtained from a subject at risk for, or suspected of having, age-associated cognitive decline or a dementing illness. The bodily sample may be obtained and then be assayed for the level of amylin. The predetermined value may be compared to the level of amylin in the bodily sample. Where the level of amylin is substantially lower than the predetermined value, it is likely that the subject has a form of age-associated cognitive decline or a dementing illness.

Additionally, a predetermined value of amylin may be compared to the level of amylin in a subject to determine the progression of age-associated cognitive decline or a dementing illness in a subject. The extent of the difference between the level of amylin in the subject and the predetermined value may also be useful for characterizing the extent of age-associated cognitive decline or a dementing illness. For example, a predetermined value comprising the level of amylin may be derived from an apparently healthy subject or population of apparently healthy subjects (as described above). A first bodily sample may then be obtained from a subject at risk for, or known to have, age-associated cognitive decline or a dementing illness and then assayed for the level of amylin. At least one other bodily sample may then be obtained and subsequently assayed for the level of amylin. The level of amylin for each of the bodily samples may then be compared to the predetermined value. Decreasing levels of amylin in the bodily samples will likely indicate a progression of age-associated cognitive decline or a dementing illness from a normal state to a diseased state.

In another aspect, a method is provided for monitoring the response to treatment of age-associated cognitive decline or a dementing illness in a subject. The level of amylin in the subject is assayed and the assayed level of amylin is correlated to age-associated cognitive decline or a dementing illness in the subject. In one method, a subject having age-associated cognitive decline or a dementing illness can be identified. The subject can be identified as having age-associated cognitive decline or a dementing illness by obtaining at least one bodily sample from the subject. For example, a bodily sample comprising blood may be obtained from the subject and then processed to plasma. The bodily sample may then be assayed for the level of amylin, as described above.

At least one treatment modality may be administered to the subject before or after detection of age-associated cognitive decline or a dementing illness. An example of a treatment modality may include the administration of amylin and/or leptin. Treatment modality can also include a therapeutic agent that is administered to the subject for treating age-associated cognitive decline or a dementing illness.

After at least one therapeutic modality has been administered, a bodily sample can be obtained from the subject and then assayed to determine the level of amylin. After the level of amylin in the bodily sample has been determined, this level may then be compared to a predetermined value, such as level of amylin in a bodily sample obtained from the subject prior to administration of the treatment modality. If the level of amylin in the sample is higher than the predetermined value, then the therapeutic modality has likely provided a therapeutic effect against age-associated cognitive decline or a dementing illness. Alternatively, if the level of amylin in the sample is lower than the predetermined value, then the therapeutic modality has likely not provided a therapeutic effect against age-associated cognitive decline or a dementing illness.

In addition to monitoring the response of a subject with age-associated cognitive decline or a dementing illness to a treatment, it may also be useful to determine an effective amount of an agent, such as amylin and/or leptin, for treating age-associated cognitive decline or a dementing illness. By monitoring the level of amylin in a subject during or following administration of a therapeutic agent, an effective amount of the therapeutic agent can be determined.

An effective amount of a therapeutic agent may include a dosage sufficient to provide a medically desirable result in a subject having a particular disease or condition. The effective amount will vary with the particular disease or condition being treated, the age and physical condition of the subject being treated, the severity of the condition, the duration of the treatment, the nature of any concurrent therapy, the specific route of administration, and the like factors within the knowledge and expertise of the health practitioner. For example, an effective amount can depend upon the degree to which an individual has abnormally reduced levels of amylin. Alternatively, an effective amount can be that amount which increases the levels of amylin. It will be recognized that when the therapeutic agent is used in acute circumstances, it can be used to prevent one or more medically undesirable results that typically flow from such adverse events. It is expected that dosages will range depending on the method of administration. In the event that a response in a subject is insufficient at the initial dosages applied, higher dosages (or effectively higher dosages by a different, more localized delivery route) may be employed to the extent that patient tolerance permits. Multiple dosages per day are contemplated to achieve appropriate systemic levels of the therapeutic agent.

The following example is included to demonstrate an embodiment of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In this Example, we measured baseline circulating plasma amylin levels in a large cohort of Alzheimer's disease (AD), mild cognitive impairment (MCI), and normal aging subjects. To further study the relationship between the hormone amylin and AD, we investigated if administration of the amylin analogue pramlintide has neuroprotective effects in a senescence-accelerated mouse (SAMP8) 1 a model increasingly being validated as a model of sporadic AD. Pramlintide acetate (Symlin, Amylin Pharmaceuticals) is an approved diabetes medication that has been well-studied in an elderly population, is generally well-tolerated, and may be safely administered to normoglycemic patients. In this study, we demonstrate for the first time an association between low amylin levels and AD. Furthermore, here we show that amylin has potent neuroprotective and neuroplastic effect and the ability of chronic administration of pramlintide to protect from the to enhance that improve cognitive function in the SAMP8 mouse.

Materials and Methods

Human Amylin Plasma Analysis

All subjects were community-based volunteers who were individually recruited to participate in plasma donation and cognitive evaluation at the University of Pennsylvania's Center for Neurodegenerative Disease Research. Written and verbal informed consent was obtained from all study participants at the time of enrollment. Subjects were eligible to participate if they were above 50 years of age and in generally good health. All subjects underwent cognitive and neurological examinations at subspecialty clinics at the University of Pennsylvania that are dedicated to the evaluation of neurodegenerative disorders. Of the 450 participants who were initially enrolled in our study, 69 participants were found to have cognitive impairment primarily due to a condition other than AD or amnestic MCI and were excluded from analysis (e.g., psychiatric, frontotemporal dementia, Lewy body dementias, medication-induced). Remaining subjects were classified into principle neuropathologic diagnosis groups according to established criteria: normal aging, mild cognitive impairment (MCI), or Alzheimer disease (AD).

Blood samples were obtained during initial clinical evaluation or at a scheduled time for biofluid donation for research purposes. All samples were collected during the daytime without prior overnight fasting. Plasma was collected in 10 mL BD Vacutainer®K2EDTA tubes and centrifuged at 4° C. into plasma and cellular components. Plasma was subsequently stored at −80° C. in 1 mL polypropylene vial aliquots until the time of analysis.

A commercial enzyme-linked immunosorbent assay (ELISA) kit (Millipore® Human Amylin ELISA) was used to determine the concentration of amylin following standard ELISA kit procedures. The ELISA capture antibody recognizes amylin and deamidated amylin (1-20 fragment), but not reduced amylin. A 4-parameter logistic equation was used for the dose-response curve of this assay. The lower sensitivity limit of the assay was 1 pM and the interassay coefficient of variation ranged from 3.7% to 6.9%.

Animals and Drug Treatment

The senescence-accelerated prone (SAMP8) mouse was selected as a model of age-related AD because it displays multiple features of AD pathogenesis including severe deficits of learning and memory. SAMP8 and SAM-resistant 1 (SAMR1) mice were obtained from an established colony at Case Western Reserve University. All animals were group housed, provided ad libitum access to a standard diet and water, and were exposed to a 12/12 light/dark daily cycle. The mice were housed under pathogen-free conditions at a temperature of 21±1.5° C.

All SAMP8 mice were treated with either saline or pramlintide beginning at 6 months of age. A subcutaneous ALZET® osmotic minipump (Model 2002, Durect Corp., Cupertino, Calif., USA) was surgically implanted into all mice as described previously[26]. The osmotic mini-pump infused 0.24 mg/kg/day pramlintide acetate (0.6 mg/mL pramlintide, Amylin Pharmaceuticals, Inc., San Diego, Calif.) or saline at a rate of 0.5 µL/hr. Pumps were replaced with new refilled pumps every two weeks throughout the study duration. All animals were weighed weekly throughout the course of the experiment.

Object Recognition Task

A total of 20 SAMP8 mice were used in the object recognition task. Half of the mice (n=10) received pramlintide infusions for five weeks, while the other half (n=10) received saline infusions. Behavioral testing occurred during the last week when the mice were 7 months old. The object recognition task was performed as described previously[27]. The testing set-up involved four adjacent open-field boxes measuring 20"×20"×17"×4" (San Diego Instruments, San Diego, Calif.) illuminated by indirect dim lighting. On the day prior to testing, mice were individually placed in one of the boxes for 15 minutes for habituation and to measure baseline locomotor activity. The following day during the training session, the mice were again placed into one of the boxes but this time with two plastic sample objects approximately 12" apart. The mice were allowed to explore the environment for 10 minutes, during which their movements were recorded with a tracking system. The box in which animals were placed was counterbalanced by treatment to avoid location bias. After each trial, the objects and open-field were cleaned with 70% ethanol to eliminate any olfactory cues. Three hours later during the retention test, the mice were once again placed in the open-field, but this time a novel object of similar size and complexity replaced one of the objects that was present during the training session. The mice were allowed to explore the environment for 5 minutes, after which they were returned to their cages.

Videos recordings of the retention session were scored by an investigator blinded to the treatment groups. Object exploration, defined as the duration of time in which the head of the mouse faced less than ½ cm from the object, was measured during the training and retention sessions. The frequency of object exploration was also recorded, as well as the frequency and time spent rearing and grooming to determine general exploratory behavior. Mice that spent less than 5 seconds total exploring the objects and mice that exhibited stereotypic behavior such as spinning were discarded from the analysis. The recognition index was calculated as the percent of time spent exploring the novel object versus the total time spent exploring the objects.

Protein Extraction and Western Blotting

All SAMP8 mice were sacrificed by lethal overdose 5 weeks after the initiation of the pramlintide and saline treatments. The brains were harvested and the hippocampus was dissected and homogenized in protease and phosphatase inhibitor-supplemented 1×RIPA lysis/extraction buffer (Pierce). Total protein was quantified using the BCA Protein Assay Kit (Pierce). 10-20 µg of protein was run in a 10% SDS-PAGE gel and the protein was transferred onto Polyvinylidene fluoride (PVDF) membranes (Millipore). After blocking for one hour in 5% milk, the membranes were incubated overnight at 4° C. in the primary antibody at a 1:1000 dilution, followed by a 1-hour incubation with HRP-conjugated IgG at a 1:10,000 dilution. Primary antibodies used were CDK5 (Millipore), P35/P25 (Millipore), Synapsin I (Santa Cruz), and HO-1 (Gift from Dr. Zhu). The blots were developed using Immobilon Western Chemiluminescent HRP Substrate (Millipore) and imaged using Fluor Chem M (ProteinSimple). Membranes were stripped using Restore Western Blot Stripping Buffer (Thermo Scientific) for reprobing. Quantifications were performed using ImageJ software.

BrdU Immunostaining

To determine the acute effects of pramilide on potential mechanisms associated with cognitive function a total of 12 control mice (SAMR1) 9 months of age were used to measure the effects of pramlintide on hippocampal neurogenesis. Half of the mice (n=6) were infused by minipump with pramlintide for a total of two weeks, while the other half (n=6) received minipumps filled with saline. For the last seven days of the experiment, all mice received daily intraperitoneal injections of 50 mg/kg BRDU (Sigma, St Louis, Mich.) dissolved in 0.9% saline. One day after the last BRDU injection, mice were deeply anesthetized and transcranially perfused using 4% paraformaldehyde in 0.9% saline. The brains were then extracted and post-fixed in 4% paraformaldehyde for 24 hours, after which they were placed in a 30% sucrose solution for three days. All brains were quick-frozen and then cut into 40 μm sagital sections using a cryostat and stored at 4° C. as floating sections.

BRDU immunohistochemistry was performed as previously described. Floating sections were initially incubated in 1% $H_2O_2$ for 1 hour to block endogenous peroxidase, followed by a pre-treatment in 1.5 N HCl+3% NGS+0.5% Triton for 1 hour at 37° c. Sections were then blocked in 3% NGS+0.5% Triton for 1 hour, and then incubated with the primary anti-BRDU antibody (Accurate Chemical #6) at a 1:2000 dilution in 3% NGS+0.3% Triton in PBS for 72 hours at 4° c. Next, the sections were placed in the secondary antibody (Biotinylated Anti-Rat IgG, Vector Lab) at a 1:500 dilution in 1.5% NGS for 1 hour at room temperature, followed by an incubation in ABC reagent for 1 hour. This was followed by a quick wash in H20, and then a 1-2 minute incubation using the chromatogen diaminobenzidine (DAB) Vector Kit (Vector Labs). Once stained cells became visible, the reaction was stopped using water, and the slices were mounted onto slides. A validated stereology protocol was used to quantify BrdU-labeled cells in the dentate gyrus. An experimenter blinded to the treatment groups performed all the cell counting at 40× under a light microscope. All BrdU-positive cells in the dentate gyrus of the hippocampus were counted in every 6th section through the hippocampus, for a total of 12 sections per animal. Cells in the outermost plane of focus were omitted. The number of BrdU-positive cells per slice were multiplied by 6 to obtain the total number of BrdU-positive cells per dentate gyrus.

Cellular Stress Immunohistochemistry

To determine whether pramilide had more acute neuroprotective effects in non-pathological conditions, sections from the same mice used for neurogenesis were used to determine markers of cellular stress. One hippocampal section was selected from each mouse (n=6 per group) and were stained with 4-Hydroxynonenal (HNE) and cyclooxygenase 2 (COX-2) at a 1:200 dilution overnight. The immunohistochemistry was performed as described for the BrdU immunostaining except there was no HCl pre-treatment.

Tissue sections were quantified. Briefly Images for all sections were captured using a light microscope and normalized for background intensity. Six fields across the hippocampus were drawn and % staining within that field was measured using Metamorph software. Data is presented as % staining/field.

Statistical Analysis

For the human plasma analysis, amylin levels had a skewed distribution to the left and were therefore logarithmically transformed for all statistical analyses and are reported as log-transformed values. The associations of amylin with demographic, clinical and potential confounder variables were examined using Pearson's correlations for continuous variables and analysis of variance (ANOVA) for categorical variables. Multinomial logistic regression analysis was used to determine the relationship between logarithmically transformed amylin level and disease category membership, with adjustment for age, sex and education. Data from mouse studies, including the object recognition task, neurogenesis, and western blot, were analyzed using a Student's t-test. All statistical analyses were performed using JMP® 9.0 for Windows (SAS Institute Inc.) P-values <0.05 were considered significant and all statistical tests were two-sided.

Results

Circulating Plasma Amylin is Reduced in Human Subjects with MCI or AD

Circulating plasma amylin levels were measured in 206 subjects with AD, 64 subjects with MCI, and 111 subjects with normal aging. Demographic and clinical characteristics of the participant groups are displayed in Table 1. As expected, there were significant differences in the clinical characteristics of the participant groups. The average plasma amylin for all patients in our study was 0.77 (SD=0.69). There was no significant association between plasma amylin concentration and age ($F_{[1,279]}$=0.021, p=0.88), sex ($F_{[1,379]}$=1.45, p=0.22), or years of education ($F_{[1,379]}$=0.0063, p=0.94).

TABLE 1

Table 1 Demographic and clinical characteristics of the participant groups.

|  | AD | MCI | Normal Aging |
|---|---|---|---|
| N | 212 | 64 | 125 |
| Age | 74.7 | 71 (8.6) | 70.2 (10.0) |
| Female Sex | 127/59.9% | 34/53.1% | 86/68.8% |
| Years of Education | 13.9 (4.0) | 13.0 (5.4) | 15.6 (3.5) |
| APO E4+ | 127/59.9% | 29/45.3% | 31/25.4% |
| MMSE annualized decline | 2.4 (2.7) | 0.91 (1.3) | 0.18 (0.38) |

Using multivariable regression analysis, we compared plasma amylin levels across the diagnostic groups with adjustment for age, sex, and education. Plasma amylin levels were significantly lower in the AD group ($F_{[4,311]}$=2.51, p=0.012) and the MCI group ($F_{[4,170]}$=2.57, p=0.0109) than the normal aging group (FIG. 1). There was no significant difference in amylin levels between the MCI and AD groups ($F_{[4,264]}$=1.01, p=0.31). We repeated these multivariable regression analyses, with additional adjustment for traditional risk factors for AD including apolipoprotein E4, diabetes, hypertension, and hyperlipidemia. Plasma amylin levels were positively associated with the apolipoprotein E4 genotype ($F_{[1,376]}$=4.17, p=0.0418). There was a trend towards higher plasma amylin levels among subjects with diabetes ($F_{[1,307]}$=3.00, p=0.084), and no association between plasma amylin and hypertension ($F_{[1,307]}$=0.17, p=0.67) or hyperlipidemia ($F_{[1,307]}$=0.003, p=0.95) was found. After additionally adjusting for all of these possible covariates, plasma amylin levels remained significantly lower in the AD group ($F_{[1,245]}$=2.05, p=0.041) and the MCI group ($F_{[1,150]}$=3.13, p=0.0021) than the normal aging group
Low Plasma Amylin is Associated with Cognitive Decline Subjects with a baseline clinical diagnosis of AD, MCI, or normal aging in the cross sectional study were followed longitudinally for a mean follow up of 2.1 years (range 1-3 years) to determine the relationship between baseline amylin concentration and the prospective risk of cognitive decline. As expected, subjects with a baseline diagnosis of AD demonstrated significant cognitive decline over the follow up period. The AD group had an average annualized MMSE score decline of 2.4, as compared to a decline of 0.91 for the MCI group and 0.18 for the normal aging group. These differences in MMSE decline adjusted for age, sex, and education were statistically significant ($F_{[5,394]}$=55.9, p=0.0001).

Across the study sample, baseline plasma amylin adjusted for age, sex, and education was significantly and inversely associated with cognitive decline as assessed by MMSE ($F_{[4,375]}$=1.41, p=0.0417). The association between low baseline plasma amylin and MMSE score decline remained significant after additionally adjusting for apolipoprotein E4, diabetes, hypertension, and hyperlipidemia ($F_{[4,371]}$=2.53, p=0.012). In post-hawk tests we also studied the association between low plasma amylin adjusted for age, sex, and education and changes in multiple cognitive domains. Among tested cognitive domains, low plasma amylin was most strongly associated with changes in executive function (F$_{[4,259]}$=2.22, p=0.027).
Pramlintide Improves Object Recognition Memory in SAMP8 Mice To investigate the effects of pramlintide on memory, SAMP8 mice were continually infused with saline or pramlintide for a total of five weeks. Consistent with pramlintide's known anorexic effect, the pramlintide-treated mice experienced a change in body weight of −5.8% (Std=4.7) over the course of the treatment period as compared to a weight change of −0.1% (6.1) for the saline-treated mice. This difference in weight loss between the two groups was statistically significant (t=2.54, p=0.019) (data not shown).

Figure 2A:
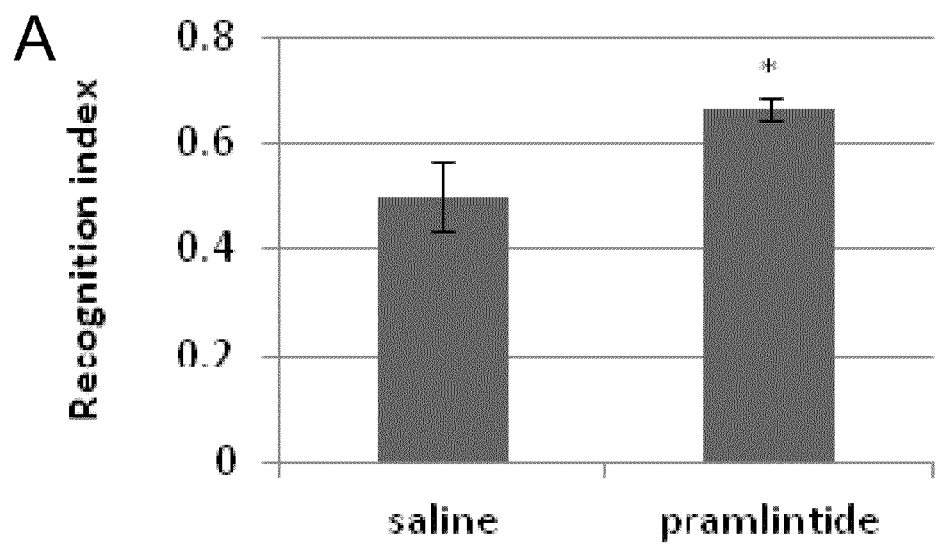
FIGS. 2A-B illustrate graphs showing the effect of pramlintide on the performance of 7-month SAMP8 mice in the Object Recognition Task. Chronic treatment of SAMP8 mice with pramlintide significantly increased recognition memory in the object recognition task compared to saline-treated controls. Recognition memory is reflected by the (A) recognition index, which is the ratio of time spent exploring the novel object relative to the total time exploring the objects. (B) The difference score is the difference in time spent exploring the new and old object divided by the total time spent exploring. The results are depicted as mean±SEM. (Student's t-test, * $p<0.05$; n=9 per group).
Figure 2B:
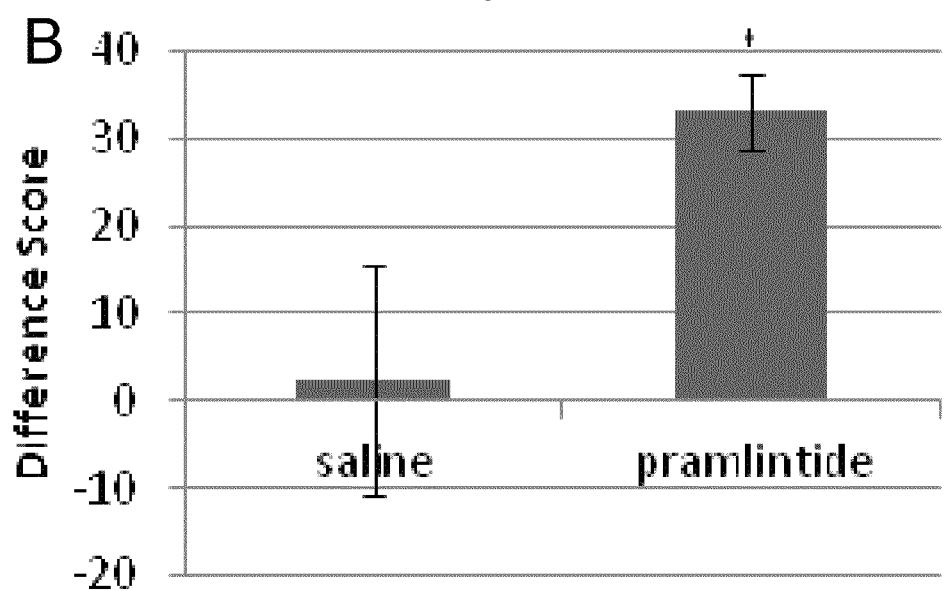
Figure 3:
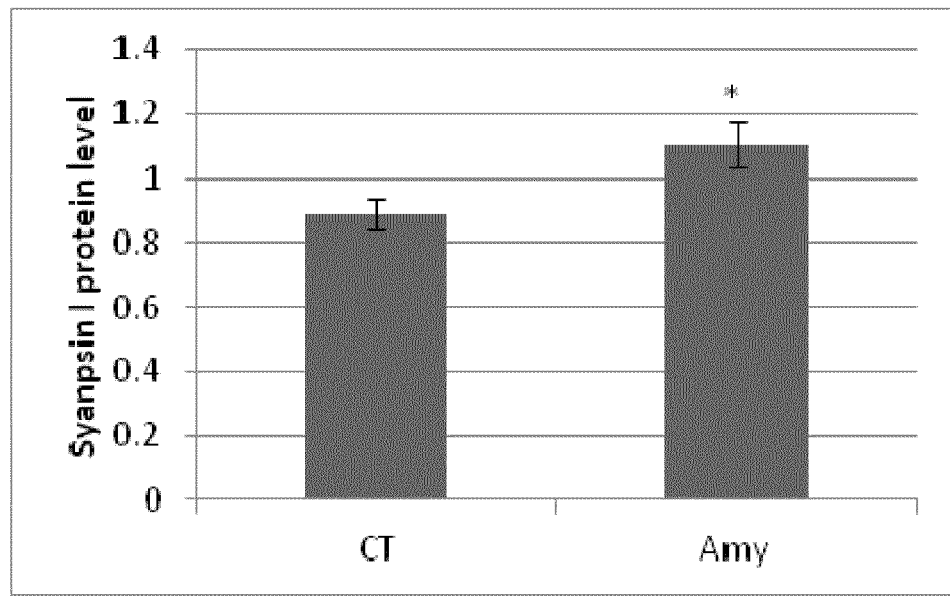
FIG. 3 illustrates a graph showing the effect of pramlintide on hippocampal synapsin I protein expression in 7-month SAMP8 mice. Chronic pramlintide treatment significantly increases synapsin I in the hippocampus of SAMP8 mice compared to saline-treated controls. The results are depicted as mean±SEM. (Student's t-test, * $p<0.05$, (n=9 for each group).
Figure 4A:
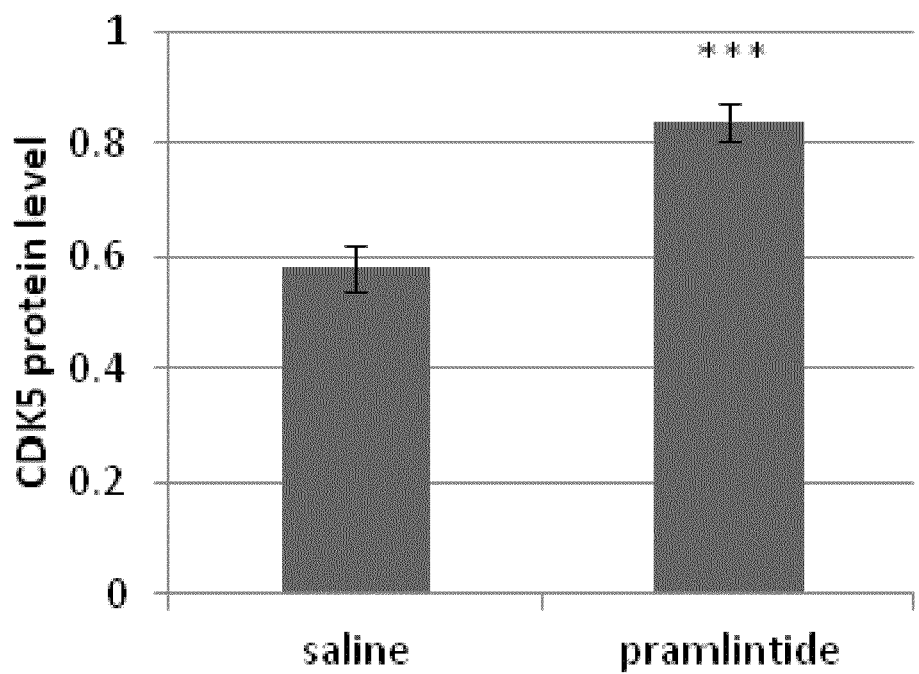
FIGS. 4A-B illustrate the effect of pramlintide on hippocampal CDK5 expression and activity level in 7-month SAMP8 mice. (A-B) Chronic treatment with pramlintide increased total CDK5 protein expression in the hippocampus (C-E) Pramlintide treatment did not have a significant effect on p35, p25, or the p25/35 ratio (p>0.05). The results are depicted as mean±SEM. (Student's t-test, *** $p<0.001$; n=7-10 per group).
Figure 4B:
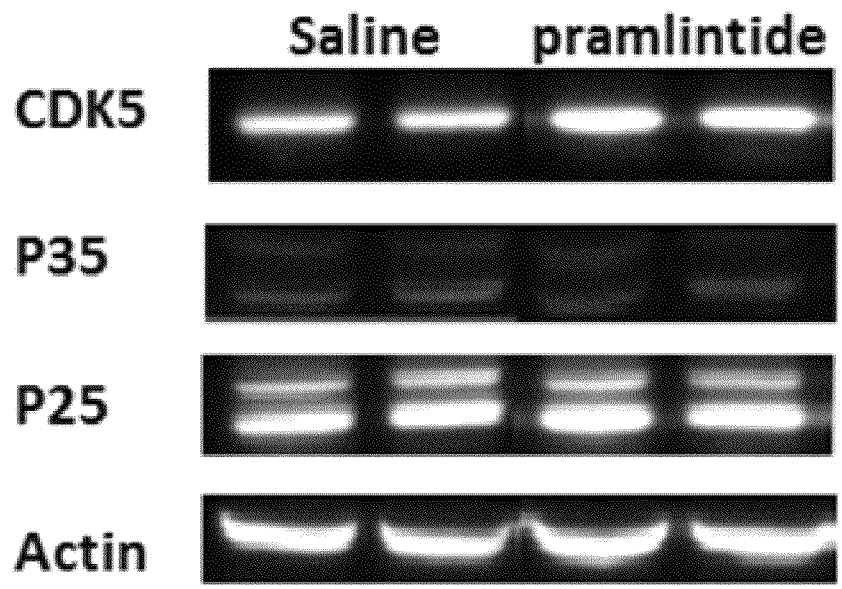
Figure 4C:
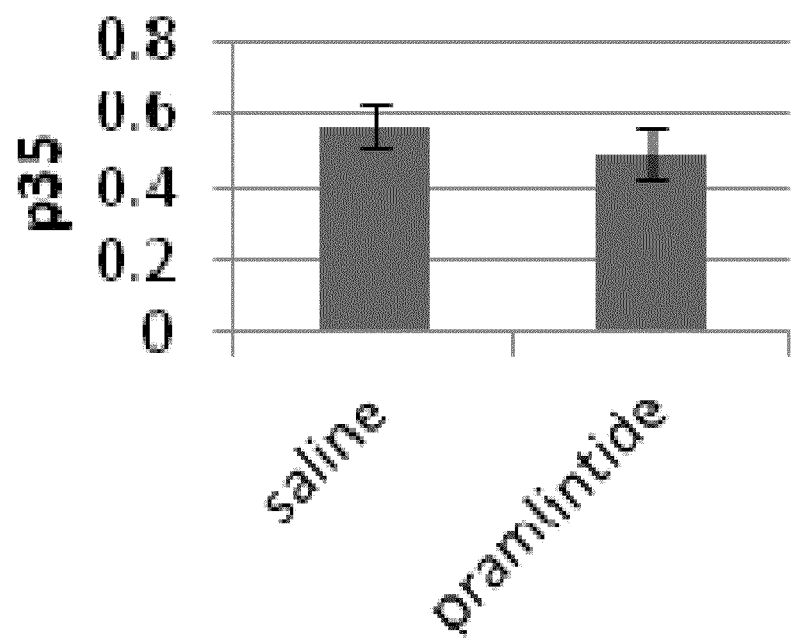
Figure 4D:
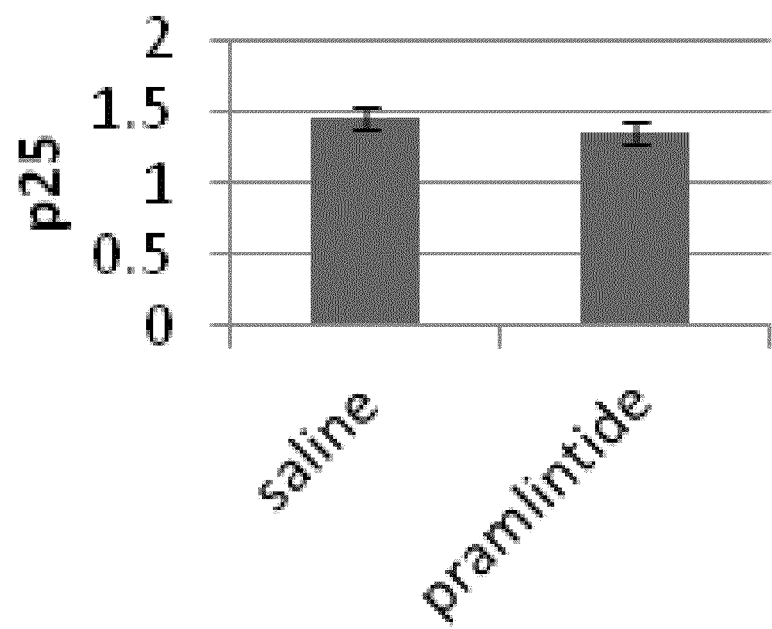
Figure 4E:
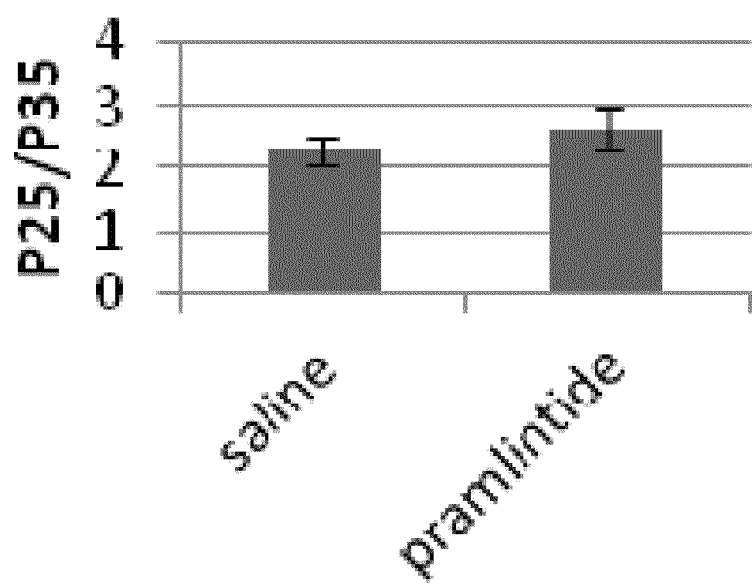
Figure 5A:
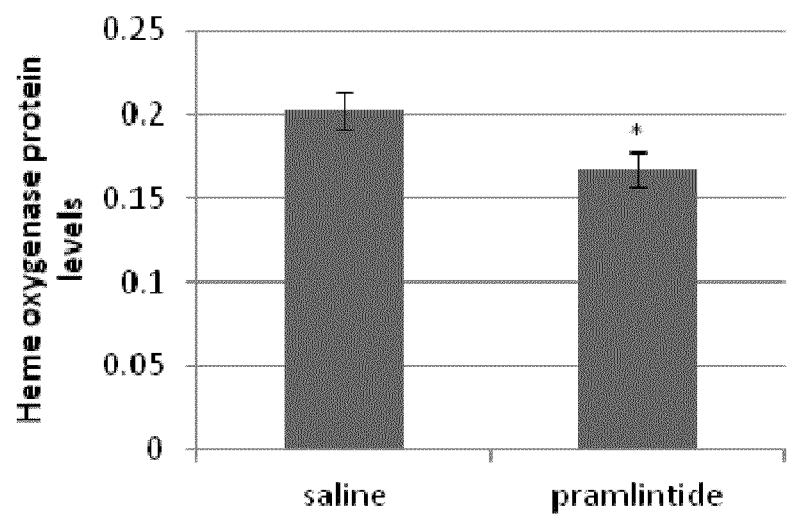
FIGS. 5A-B illustrate the effect of chronic pramlintide on hippocampal HO-1 protein expression. Chronic pramlintide treatment for 5 weeks significantly decreased HO-1 protein levels in the hippocampus of 7-month SAMP8 mice. The results are depicted as mean±SEM. (Student's t-test, * $p<0.05$; n=9 per group).
Figure 5B:
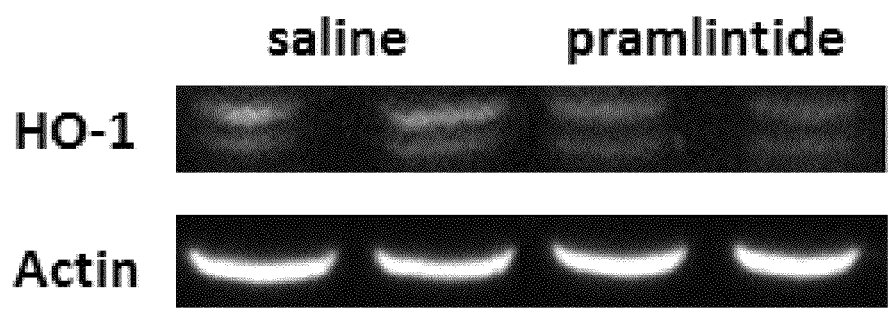
Figure 6A:
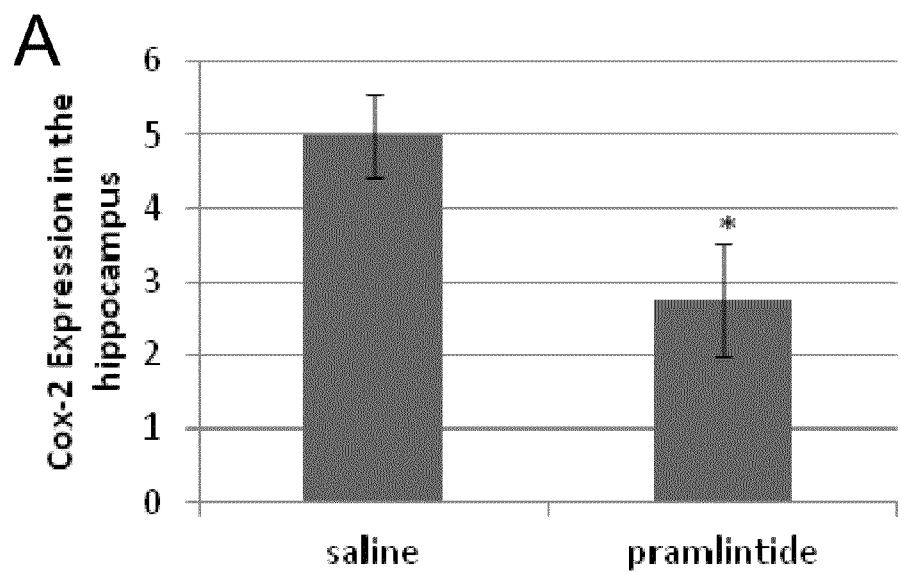
FIGS. 6A-B illustrate graphs showing effect of chronic pramlintide on hippocampal HNE and COX-2 expression.
Figure 6B:
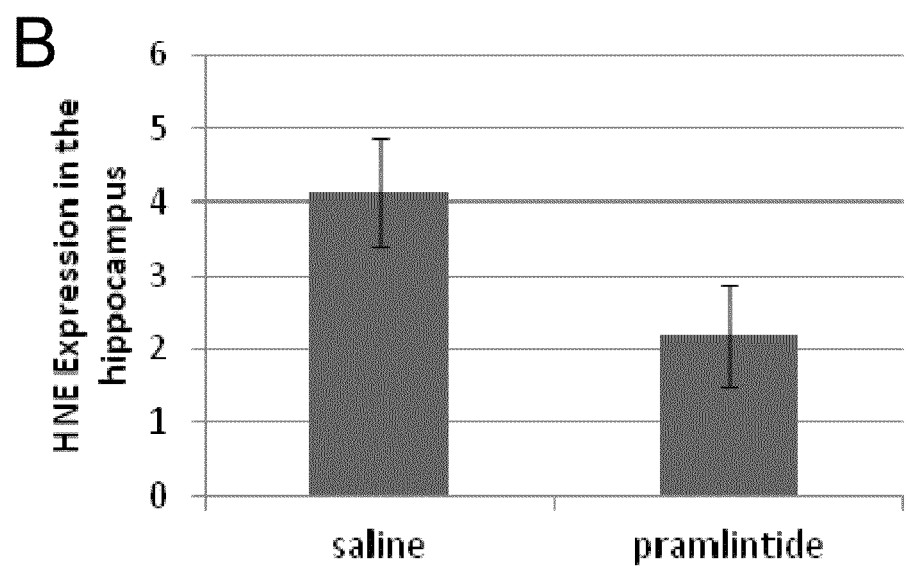
Figure 7:
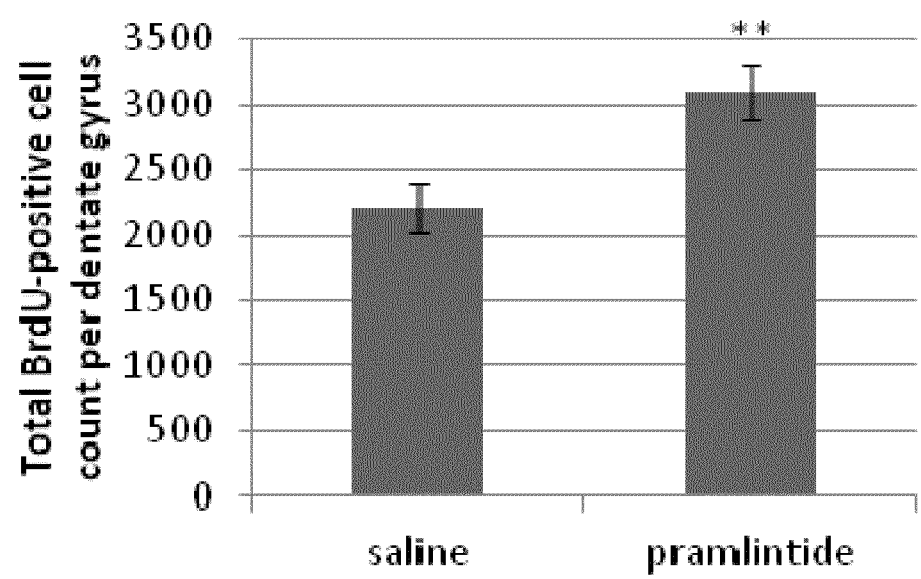
FIG. 7 illustrates a graph showing the effect of pramlintide on neurogenesis in the dentate gyrus of 9-month SAMR1 mice.

During the last week of treatment, all mice were tested in the object recognition task to investigate pramlintide's effects on memory. The object recognition task takes advantage of the natural tendency of mice to explore a novel object more than a familiar object to evaluate recognition memory. The pramlintide-treated SAMP8 mice spent a greater proportion of time exploring the novel objects as compared to the familiar objects, whereas the saline-treated SAMP8 mice were unable to discriminate between the novel and familiar objects. The recognition index for pramlintide-treated mice was 0.67 (Std=0.06), as compared to 0.50 (0.20) for the saline treated mice, a difference that was statistically significant (FIG. 2, t=2.40, p=0.029). There was no difference in exploratory behavior, as measured by time spent rearing (t=1.14, p=0.27) or grooming (t=0.39, p=0.70), between the pramlintide- and saline-treated groups.
Pramlintide Increases Synaptic Proteins and CDK5 Expression in the Hippocampus Hippocampal tissue from the SAMP8 mice treated with pramlintide for five weeks was examined by western blotting technique to determine what proteins are altered by pramlintide that may underlie its neuroprotective effects. Pramlintide was found to significantly increase hippocampal expression of synapsin I (FIG. 3), a protein located in neuronal synaptic vesicles that can be used as a marker of synaptic density (t=3.38, p=0.0042). To investigate a potential mechanism underlying pramlintide's effects on synaptic density, we explored the possibility that pramlintide may alter CDK5, a protein that is strongly implicated in both neuron and synapse growth and is modulated by many growth factors. In the hippocampus of SAMP8 mice treated with pramlintide for five weeks, expression of the protein CDK5 was significantly increased relative to the saline-treated group (FIG. 4A-B, t=5.01, p=0.002). There were no differences in the amount of the CDK5 activator p35 (t=0.64, p=0.53), its cleavage product p25 (t=0.22, p=0.83), or the ratio of p25/p35 (t=0.85, p=0.41) (FIG. 4C-E).
Pramlintide Reduces Markers of Oxidative Stress and Inflammation To begin to determine whether pramlintide has insult-related neuroprotective effects, we used western blotting to quantify levels of HO-1, a well-known stress-related enzyme that is a sensitive marker of oxidative stress. Pramlintide-treated SAMP8 mice showed significantly decreased expression of the protein HO-1 in the hippocampus compared to saline-treated mice, a difference that was statistically significant (FIG. 5) (t=2.31, p=0.035). To further explore the effects of pramlintide on oxidative stress and inflammation, we used immunostaining to quantify levels of cyclooxygenase-2 (COX-2) and 4-Hydroxynonenal (HNE), two other markers of inflammation and cellular stress. We demonstrate significant decreases in COX-2 immunostaining (p=0.042) and a trend toward decreased HNE immunostaining (p=0.090) in the hippocampus of mice treated with pramlintide for 2 weeks compared to saline-treated mice (FIG. 6).
Pramlintide Increases Hippocampal Neurogenesis To investigate the possibility that increased neurogenesis may mediate the memory-enhancing properties of pramlintide, we used BrdU labeling to quantify neurogenesis in the hippocampus of pramlintide-treated mice. The pramlintide-treated mice had 40% more BrdU-positive cells in the dentate gyrus compared to saline-treated mice (FIG. 7A-C), a difference that was statistically significant (t=3.23, p=0.0090).

Example 2

In this Example, we examined whether chronic amylin administration has beneficial effects on cognition using senescence-accelerated SAMP8 mice, a validated animal model of mild cognitive impairment (MCI)/early Alzheimer's disease (AD) in which the mice experience premature cognitive deficits. Given that the anorectic effects of amylin are specifically synergistic with another metabolic hormone, leptin, we also studied whether amylin's effects on cognition might be enhanced when used in conjunction with leptin.

The mechanisms of amylin signaling have not been completely elucidated. Nevertheless, amylin binds with high affinity to the calcitonin/gene related peptide (CT/CGRP), mediated by the receptor-activity modifying protein 1 (RAMP1) in the hippocampus and cortex. Amylin receptor activation leads to increases in intracellular levels of cAMP, which have been demonstrated to induce synapsin I expression through EGR-1 transcription activation. Furthermore, amylin receptor signaling increases intracellular Ca2+ stores, capable of auto-phosphorylating calcium/calmodulin-dependent protein kinase II and ERK phosphorylation in hypothalamic cells. It has also been shown that both CaMK11 and ERK proteins require the presence of synapsin I as a substrate to carry on the different biochemical processes involved in neuronal activity and memory formation.

Amylin's effects on cognition may also be mediated through histamine. It is known that histamine release and receptor binding leads to increases in neurotransmitters such as acetylcholine, which is critical to cognitive function. In this regard, administration of amylin in combination with acetylcholinesterase inhibitors can also provide additional benefits that those of acetylcholinesterase inhibitors alone. Importantly, several studies have demonstrated a neuronal histamine deficit in Alzheimer's disease, and drugs that increase histamine levels in the central nervous system, such as histamine H3 receptor antagonists, have shown therapeutic potential for the symptomatic treatment of Alzheimer's disease. Evidence linking amylin to the histeminergic system includes the fact that amylin and histamine cells are localized to the same brain regions and amylinergic neurons contain histaminergic receptors. Furthermore, the histamine H3 agonist thioperamide (which reduces CNS histamine levels) abolishes amylin's anorectic effects.

Given that these signaling molecules and receptors are associated with processes of synaptic plasticity, learning and memory, the fact that amylin receptors are found in cognition-related regions (same as the leptin receptor), that amylin bins in key regions associated with the production of cognition-related neurotransmitters such as acetylcholine, and the fact that the leptin receptor is known to directly modulate similar cognition-associated pathway, we believe that amylin alone will have an impact on cognitive processes and associated molecular signaling pathways that will be further amplified by the addition of leptin and acetylcholinesterase inhibitors.

Figure 8:
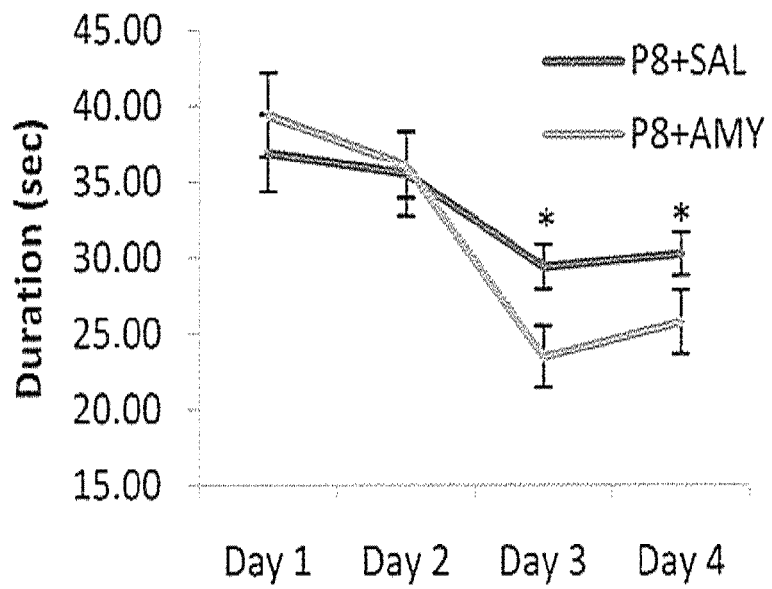
FIG. 8 illustrates MWM learning task. Amylin (AMY) treated P8 show improved learning over non-treated P8 animals. *=P8+AMY statistically SIGNIFICANT FROM P8+SAL.
Figure 9:
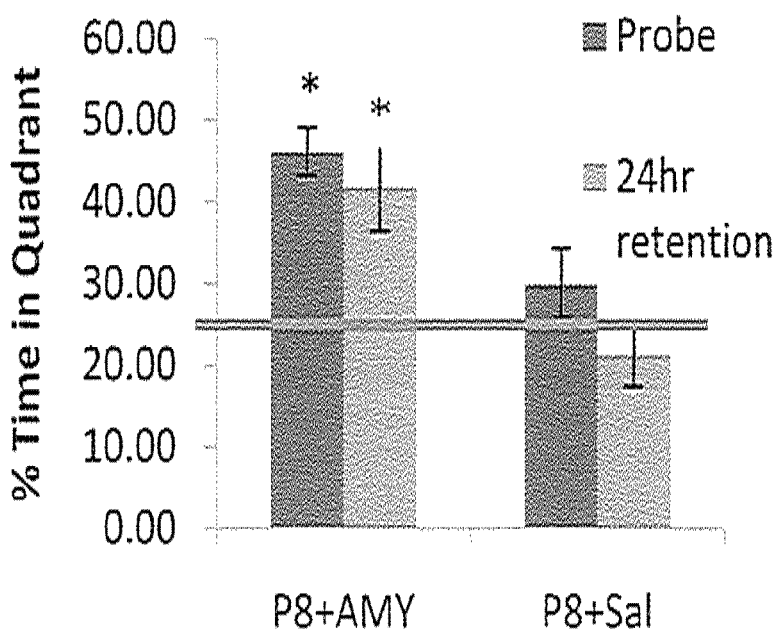
FIG. 9 illustrates probe and retention trials. AMY treated P8 show improved use of spatial strategy (probe) and improved retention over non treated P8. *=P8+AMY statistically significant from P8+SAL.

To validate the hypothesis that amylin is a cognitive enhancing drug that can be given alone and that may provide benefit for cognitive dysfunction associated diseases such as AD or age-related cognitive dysfunction (normal or Mild cognitive impairment (MCI)), we determined the ability of chronic treatment with amylin to improve cognitive function in the Morris water maze and object recognition tasks in the age accelerated SAMP8 mouse model, a model of MCI/early AD. Here, we demonstrate that amylin has a potent effect on learning of the MWM task (FIG. 8). In addition, probe trial, which reflect hippocampal function specifically, shows that amylin treated animals perform better than non-treated P8. Furthermore, improvement of amylin treatment in the retention trial, carried out 24 hrs reflects the ability of amylin to improve consolidation to long-term, permanent memory. (FIG. 9). Taken together these data indicate that amylin has a powerful beneficial effect on hippocampal-driven function, a region affected by aging and devastated in AD.

Figure 10:
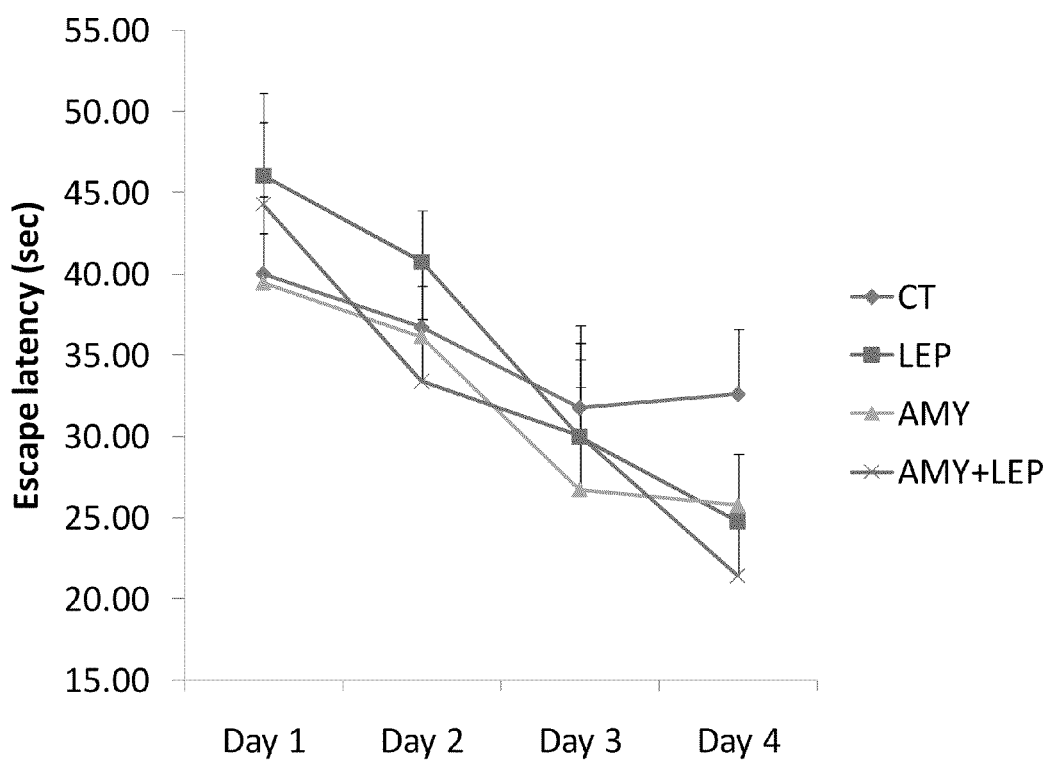
FIG. 10 is a plot illustrating Morris water maze probe and retention trails under long treatment of AMY, and acute treatment of leptin (LEP) in SAMP8 mice.
Figure 11:
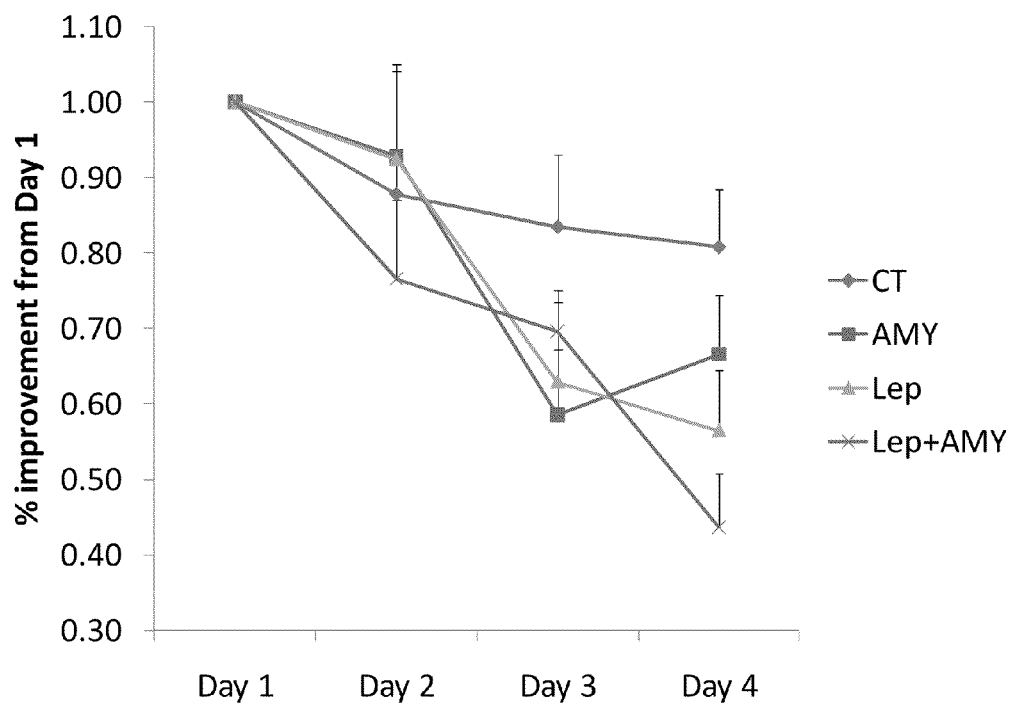
FIG. 11 is a plot showing % improvement from day 1 of SAMP8 mice treated as in FIG. 10.
Figure 12:
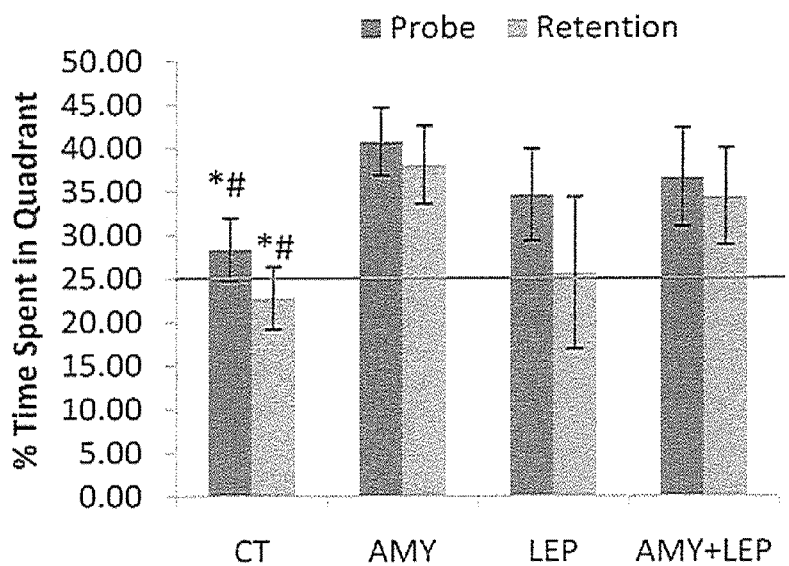
FIG. 12 illustrates Morris water maze probe and retention trials under long treatment of AMY, and acute treatment of LEP in SAMP8 mice.
Figure 13:
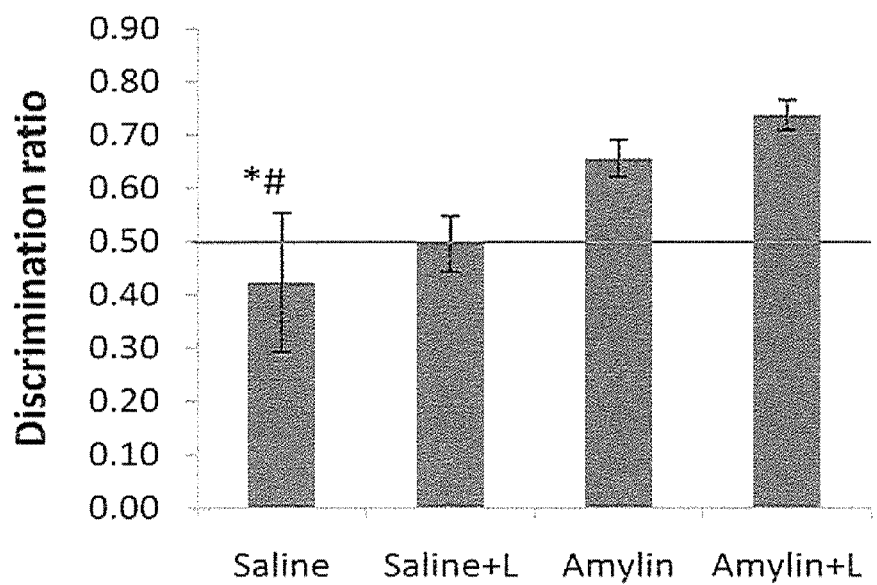
FIG. 13 illustrates novel object recognition performance of animals under saline, chronic treatment of AMY, acute treatment of LEP and chronic AMY+acute LEP in SAMP8 mice. Performance below red line shows impairment. (CT (saline) statistically significant impairment from AMY(*) and AMY+ LEP(#)).

We have also shown that the combination therapy (amylin+leptin) is more effective than single therapy alone (leptin or amylin). We were able to test this hypothesis under chronic amylin treatment and acute delivery of leptin at time of testing in SAMP8 mice. FIGS. 10 and 11 shows that MWM maze learning was observed in all groups but was improved by amylin and leptin as well as the combination treatment, which showed the best performance. The slope of the curve for the control SAMP8 mice administered saline did not change across the days. The slope of curve for the SAMP8 mice treated with a combination of amylin and leptin was the steepest so the magnitude of improvement is much larger compared to the use of either leptin or amylin administered alone. FIG. 12 demonstrates that treatments improved hippocampal function in the probe trial and retention trial when compared to saline treatment suggesting better hippocampal function both by ability to search spatially (probe) and to consolidate memories into long-term storage (retention). Novel object recognition testing, another cognition-based test, supported our findings in the MWM. As shown in FIG. 13, amylin and amylin+leptin (leptin delivered acutely) treatment in SAMP8 mice, performed significantly better (above 0.5 discrimination ratio) than saline treated animals. Interestingly, leptin treatment alone was the weakest treatment in both tasks and showed no benefits in probe/retention trials of MWM and on the novel object recognition task. This suggests that at least when delivered acutely in models of cognitive dysfunction, leptin is not effective. It is important to note that these studies were carried out in cognitively impaired animals with leptin treatments under acute conditions. As such, it is likely that the lack of observable synergistic additive magnitude derives from insufficient length of leptin treatment. However, the fact that SAMP8 animals did not show cognitive improvement with leptin alone treatment but animals with leptin+amylin showed the best performance in MWM learning and novel object recognition suggests that indeed the combination is more effective than either treatment alone if both are given chronically.

We have also found that amylin treatment may alter synapsin I and upstream targets such as ERK phosphorylation and CAMKII autophosphorylation, all of which are intimately associated with the process of learning and memory. Our behavioral studies firmly show that amylin has a strong potential to modulate cognitive function and therefore improve cognition deficits associated with aging and in neurodegenerative diseases that are associated with overt cognitive decline.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

Having described the invention, we claim:

1. A method of treating cognitive impairment or deficit associated with mild cognitive impairment or Alzheimer's disease of a subject in need thereof, comprising:
   administering to the subject a therapeutically effective amount of amylin, an amylin agonist, or an amylin derivative to treat the cognitive impairment or deficit of the subject.

2. The method of claim 1, wherein the amount of the amylin, amylin agonist, or amylin derivative administered to the subject is an amount effective to increase cognitive scores; improve memory; or slow the progression of dementia.

3. The method of claim 1, further comprising administering a therapeutically effective amount of leptin.

4. The method of claim 1, further comprising administering a therapeutically effective amount of an acetylcholinesterase inhibitor to the subject.

5. The method of claim 1, wherein the subject has at least one condition selected from the group consisting of obesity, insulin resistance, diabetes, hypertension, and an apolipoprotein E4 genotype.

6. A method of treating cognitive impairment or deficit associated with mild cognitive impairment or Alzheimer's disease of a subject in need thereof, comprising:
   administering to the subject a therapeutically effective amount of amylin, an amylin agonist, or an amylin derivative in combination with a therapeutically effective amount of leptin to treat the cognitive impairment or deficit of the subject.

7. The method of claim 6, wherein the amount of the amylin, amylin agonist, or amylin derivative in combination with the leptin administered to the subject is an amount effective to increase cognitive scores; improve memory; or slow the progression of dementia.

8. The method of claim 6, further comprising administering a therapeutically effective amount of an acetylcholineesterase inhibitor to the subject.

9. The method of claim 6, wherein the subject has at least one condition selected from the group consisting of obesity, insulin resistance, diabetes, hypertension, and an apolipoprotein E4 genotype.

10. A method of treating cognitive impairment or deficit associated mild cognitive impairment or Alzheimer's disease in a subject in need thereof, comprising:
    administering to the subject a therapeutically effective amount of amylin, an amylin agonist, or an amylin derivative in combination with a therapeutically effective amount of an acetylcholinesterase inhibitor to treat the cognitive impairment or deficit.

11. The method of claim 10, wherein the amount of the amylin, amylin agonist, or amylin derivative in combination with the acetylcholinesterase inhibitor administered to the subject is an amount effective to increase cognitive scores; improve memory; or slow the progression of dementia of the affected subject.

12. The method of claim 10, further comprising administering a therapeutically effective amount of leptin.

13. The method of claim 10, wherein the subject has at least one condition selected from the group consisting of obesity, insulin resistance, diabetes, hypertension, and an apolipoprotein E4 genotype.

* * * * *

SEQUENCE LISTING

```
<160> NUMBER OF SEQ ID NOS: 3

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15
```

```
Val His Ser Ser Asn Asn Phe Gly Ala Ile Leu Ser Ser Thr Asn Val
            20                  25                  30

Gly Ser Asn Thr Tyr
            35

<210> SEQ ID NO 2
<211> LENGTH: 37
<212> TYPE: PRT
<213> ORGANISM: Rattus norvegicus

<400> SEQUENCE: 2

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
            35

<210> SEQ ID NO 3
<211> LENGTH: 32
<212> TYPE: PRT
<213> ORGANISM: Homo sapiens

<400> SEQUENCE: 3

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```